(12) United States Patent
Mathies et al.

(10) Patent No.: US 8,841,116 B2
(45) Date of Patent: Sep. 23, 2014

(54) INLINE-INJECTION MICRODEVICE AND MICROFABRICATED INTEGRATED DNA ANALYSIS SYSTEM USING SAME

(75) Inventors: Richard A. Mathies, Moraga, CA (US); Robert Blazej, San Francisco, CA (US); Palani Kumaresan, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 994 days.

(21) Appl. No.: 11/978,224

(22) Filed: Oct. 25, 2007

(65) Prior Publication Data

US 2009/0035770 A1 Feb. 5, 2009

Related U.S. Application Data

(60) Provisional application No. 60/854,570, filed on Oct. 25, 2006, provisional application No. 60/881,411, filed on Jan. 19, 2007.

(51) Int. Cl.
| | | |
|---|---|---|
| *C12M 1/00* | (2006.01) | |
| *C12M 1/34* | (2006.01) | |
| *C12M 3/00* | (2006.01) | |
| *G01N 15/06* | (2006.01) | |
| *B01D 57/02* | (2006.01) | |
| *C02F 1/40* | (2006.01) | |
| *B01L 3/00* | (2006.01) | |
| *G01N 27/447* | (2006.01) | |
| *G01N 1/40* | (2006.01) | |
| *B01L 7/00* | (2006.01) | |

(52) U.S. Cl.
CPC .... *G01N 27/44743* (2013.01); *B01L 3/502784* (2013.01); *B01L 3/502753* (2013.01); *G01N 1/405* (2013.01); *B01L 2200/0673* (2013.01); *B01L 2400/0487* (2013.01); *B01L 2200/027* (2013.01); *B01L 2200/10* (2013.01); *B01L 7/52* (2013.01); *B01L 2400/0421* (2013.01); *B01L 2200/0631* (2013.01); *B01L 2300/0803* (2013.01); *B01L 3/502715* (2013.01)

USPC ... 435/283.1; 435/6.1; 435/287.2; 435/288.5; 435/288.6; 422/68.1; 204/451; 204/453; 204/604

(58) Field of Classification Search
USPC .............. 435/6.1, 283.1, 287.2, 288.5, 288.6; 422/68.1; 204/451, 453, 604
See application file for complete search history.

(56) References Cited

U.S. PATENT DOCUMENTS

| | | |
|---|---|---|
| 3,190,310 A | 6/1965 | Honsinger |
| 3,352,643 A | 11/1967 | Ando et al. |

(Continued)

FOREIGN PATENT DOCUMENTS

| | | |
|---|---|---|
| CA | 2433145 A1 | 5/2002 |
| CN | 101449089 | 6/2009 |

(Continued)

OTHER PUBLICATIONS

PCT Notification of Transmittal of the International Search Report and the Written Opinion of the International Searching Authority, or the Declaration, mailed Jun. 17, 2008, Application No. PCT/US07/82568.

(Continued)

*Primary Examiner* — Narayan Bhat
(74) *Attorney, Agent, or Firm* — Weaver Austin Villeneuve & Sampson LLP

(57) ABSTRACT

Methods and microfluidic circuitry for inline injection of nucleic acids for capillary electrophoresis analysis are provided. According to various embodiments, microfabricated structures including affinity-based capture matrixes inline with separation channels are provided. The affinity-based capture matrixes provide inline sample plug formation and injection into a capillary electrophoresis channel. Also provided are methods and apparatuses for a microbead-based inline injection system for DNA sequencing.

42 Claims, 14 Drawing Sheets

(56) References Cited

U.S. PATENT DOCUMENTS

| | | |
|---|---|---|
| 3,433,257 A | 3/1969 | Jensen |
| 3,568,692 A | 3/1971 | Metzger et al. |
| 3,610,274 A | 10/1971 | Levesque et al. |
| 3,636,334 A | 1/1972 | Svoboda |
| 3,768,521 A | 10/1973 | Brychta et al. |
| 4,304,257 A | 12/1981 | Webster |
| 4,357,675 A | 11/1982 | Freyman |
| 4,558,845 A | 12/1985 | Hunkapiller |
| 4,703,913 A | 11/1987 | Hunkapiller |
| 4,963,498 A | 10/1990 | Hillman et al. |
| 5,157,284 A | 10/1992 | O'Connell et al. |
| 5,376,252 A | 12/1994 | Ekström et al. |
| 5,453,163 A | 9/1995 | Yan |
| 5,571,410 A | 11/1996 | Swedberg et al. |
| 5,587,128 A | 12/1996 | Wilding et al. |
| 5,609,919 A | 3/1997 | Yuan et al. |
| 5,635,358 A | 6/1997 | Wilding et al. |
| 5,639,428 A | 6/1997 | Cottingham |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,842,787 A | 12/1998 | Kopf-sill et al. |
| 5,856,174 A | 1/1999 | Lipshutz et al. |
| 5,863,502 A | 1/1999 | Southgate et al. |
| 5,885,470 A | 3/1999 | Parce et al. |
| 5,900,130 A * | 5/1999 | Benvegnu et al. ............ 204/453 |
| 5,908,552 A | 6/1999 | Zimmerman et al. |
| 5,922,591 A | 7/1999 | Anderson et al. |
| 5,942,443 A | 8/1999 | Parce et al. |
| 5,971,158 A | 10/1999 | Yager et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,348,318 B1 | 2/2002 | Valkirs |
| 6,379,929 B1 | 4/2002 | Burns et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,520,753 B1 | 2/2003 | Grosjean et al. |
| 6,521,188 B1 | 2/2003 | Webster |
| 6,524,456 B1 | 2/2003 | Ramsey et al. |
| 6,532,997 B1 | 3/2003 | Bedingham et al. |
| 6,533,914 B1 | 3/2003 | Liu |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| D486,156 S | 2/2004 | Lee et al. |
| 6,685,442 B2 | 2/2004 | Chinn et al. |
| 6,705,345 B1 | 3/2004 | Bifano |
| D488,818 S | 4/2004 | Lee et al. |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,824,663 B1 | 11/2004 | Boone |
| 6,829,753 B2 | 12/2004 | Lee et al. |
| 6,852,287 B2 | 2/2005 | Ganesan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,097,809 B2 | 8/2006 | Van Dam et al. |
| 7,198,759 B2 | 4/2007 | Bryning et al. |
| 7,261,812 B1 | 8/2007 | Karp et al. |
| 7,279,146 B2 | 10/2007 | Nassef et al. |
| 7,282,361 B2 | 10/2007 | Hodge |
| 7,312,611 B1 | 12/2007 | Harrison et al. |
| 7,323,305 B2 * | 1/2008 | Leamon et al. .................. 435/6 |
| 7,438,856 B2 | 10/2008 | Jedrzejewski et al. |
| 7,445,926 B2 | 11/2008 | Mathies et al. |
| 7,488,603 B2 | 2/2009 | Gjerde et al. |
| 7,622,081 B2 | 11/2009 | Chou et al. |
| 7,745,207 B2 | 6/2010 | Jovanovich et al. |
| 7,763,453 B2 | 7/2010 | Clemmens et al. |
| 7,766,033 B2 | 8/2010 | Mathies et al. |
| 7,799,553 B2 | 9/2010 | Mathies et al. |
| 7,867,763 B2 | 1/2011 | Facer et al. |
| 8,105,553 B2 | 1/2012 | Grossman et al. |
| 8,257,666 B2 | 9/2012 | Quake et al. |
| 8,286,665 B2 | 10/2012 | Mathies et al. |
| 8,420,318 B2 | 4/2013 | Mathies et al. |
| 8,454,906 B2 | 6/2013 | Mathies et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0160361 A1 | 10/2002 | Loehrlein et al. |
| 2002/0166585 A1 | 11/2002 | O'Connor et al. |
| 2002/0187560 A1 | 12/2002 | Pezzuto et al. |
| 2003/0008308 A1 | 1/2003 | Enzelberger et al. |
| 2003/0021734 A1 | 1/2003 | Vann et al. |
| 2003/0070677 A1 | 4/2003 | Handique et al. |

(56) References Cited

U.S. PATENT DOCUMENTS

| | | |
|---|---|---|
| 2003/0217923 A1 | 11/2003 | Harrison et al. |
| 2004/0014091 A1 | 1/2004 | Duck et al. |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0197845 A1 | 10/2004 | Hassibi et al. |
| 2004/0209354 A1* | 10/2004 | Mathies et al. ............ 435/287.2 |
| 2004/0224380 A1 | 11/2004 | Chou et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0155861 A1* | 7/2005 | Guzman ...................... 204/451 |
| 2005/0161326 A1 | 7/2005 | Morita et al. |
| 2005/0161669 A1 | 7/2005 | Jovanovich et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0255003 A1 | 11/2005 | Summersgill et al. |
| 2005/0287572 A1* | 12/2005 | Mathies et al. ................... 435/6 |
| 2006/0027456 A1 | 2/2006 | Harrison et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0186043 A1 | 8/2006 | Covey et al. |
| 2006/0266645 A1 | 11/2006 | Chen et al. |
| 2007/0017812 A1 | 1/2007 | Bousse |
| 2007/0034025 A1 | 2/2007 | Pant et al. |
| 2007/0092914 A1 | 4/2007 | Griffiths et al. |
| 2007/0105163 A1 | 5/2007 | Grate et al. |
| 2007/0122819 A1 | 5/2007 | Wu et al. |
| 2007/0175756 A1 | 8/2007 | Nguyen et al. |
| 2007/0184463 A1 | 8/2007 | Molho et al. |
| 2007/0202531 A1 | 8/2007 | Grover |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0124723 A1 | 5/2008 | Dale et al. |
| 2008/0164155 A1 | 7/2008 | Pease et al. |
| 2008/0179255 A1 | 7/2008 | Jung et al. |
| 2008/0237146 A1 | 10/2008 | Harrison et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0035770 A1 | 2/2009 | Mathies et al. |
| 2009/0053799 A1 | 2/2009 | Chang-yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0181411 A1 | 7/2009 | Battrell et al. |
| 2009/0253181 A1 | 10/2009 | Vangbo et al. |
| 2009/0286327 A1 | 11/2009 | Cho et al. |
| 2009/0311804 A1 | 12/2009 | Mcbrady et al. |
| 2010/0068723 A1 | 3/2010 | Jovanovich et al. |
| 2010/0165784 A1 | 7/2010 | Jovanovich et al. |
| 2010/0224255 A1 | 9/2010 | Mathies et al. |
| 2010/0252123 A1 | 10/2010 | Mathies et al. |
| 2010/0285975 A1 | 11/2010 | Mathies et al. |
| 2010/0303687 A1 | 12/2010 | Blaga et al. |
| 2010/0326826 A1 | 12/2010 | Harrison et al. |
| 2011/0005932 A1 | 1/2011 | Jovanovich et al. |
| 2011/0020920 A1 | 1/2011 | Mathies et al. |
| 2011/0027913 A1 | 2/2011 | Bau et al. |
| 2011/0039303 A1 | 2/2011 | Jovanovich et al. |
| 2011/0048945 A1 | 3/2011 | Harrison et al. |
| 2011/0076735 A1 | 3/2011 | Jovanovich et al. |
| 2012/0142010 A1 | 6/2012 | Mathies et al. |
| 2012/0164627 A1 | 6/2012 | Battrell et al. |
| 2012/0276544 A1 | 11/2012 | Quake et al. |

FOREIGN PATENT DOCUMENTS

| | | |
|---|---|---|
| CN | 102416350 | 4/2012 |
| EP | 0459241 B1 | 12/1991 |
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 5/2004 |
| EP | 1774042 | 4/2007 |
| EP | 1345697 B1 | 6/2007 |
| EP | 1658890 B1 | 5/2008 |
| EP | 2029921 | 3/2009 |
| EP | 1345551 B1 | 4/2009 |
| EP | 2404676 | 11/2012 |
| JP | 2007/506430 A | 7/1995 |
| JP | 408327594 A | 12/1996 |
| JP | 2001/500966 | 1/2001 |
| JP | 2001/521818 A | 11/2001 |
| JP | 2002/3701200 A | 12/2002 |
| JP | 2003/516129 A | 5/2003 |
| JP | 2006-512092 | 4/2006 |
| JP | 2008-500836 | 1/2008 |
| JP | 2009-530569 | 8/2009 |
| JP | 2011-234728 | 11/2011 |
| WO | 93/22053 | 4/1993 |
| WO | WO 96/04547 A1 | 2/1996 |
| WO | 98/10277 | 3/1998 |
| WO | 98/53300 A2 | 11/1998 |
| WO | WO 98/52691 A1 | 11/1998 |
| WO | 98/53300 A3 | 2/1999 |
| WO | 99/22868 | 5/1999 |
| WO | WO 99/36766 A1 | 7/1999 |
| WO | WO 99/40174 A1 | 8/1999 |
| WO | WO 00/40712 A1 | 7/2000 |
| WO | 00/61198 A1 | 10/2000 |
| WO | WO 00/60362 A1 | 10/2000 |
| WO | 00/72970 | 12/2000 |
| WO | 2001/32930 A1 | 5/2001 |
| WO | WO 01/38865 A1 | 5/2001 |
| WO | WO 01/85341 A1 | 11/2001 |
| WO | 02/43864 | 6/2002 |
| WO | WO 02/43615 A2 | 6/2002 |
| WO | WO 02/43615 A3 | 3/2003 |
| WO | 03/085379 A2 | 10/2003 |
| WO | 03/085379 A3 | 12/2003 |
| WO | 2004/061085 | 7/2004 |
| WO | WO 2004/098757 A2 | 11/2004 |
| WO | WO 2005/075081 A1 | 8/2005 |
| WO | 2005/118867 | 12/2005 |
| WO | WO2006/032044 * | 3/2006 |
| WO | WO 2004/098757 A3 | 5/2006 |
| WO | 2007/082480 A1 | 7/2007 |
| WO | 2007/109375 | 9/2007 |
| WO | 2008/039875 A1 | 4/2008 |
| WO | 2008/052138 | 5/2008 |
| WO | 2008/115626 A2 | 9/2008 |
| WO | 2008/115626 A3 | 11/2008 |
| WO | 2009/015296 | 1/2009 |
| WO | 2009/129415 A1 | 10/2009 |
| WO | 2010/041174 A1 | 4/2010 |
| ZA | 2005/04838 | 3/2006 |

OTHER PUBLICATIONS

Hjerten, *High-Performance Electrophoresis: Elimination of Electroendosmosis and Solute Adsorption.* J. Chromatography 347: 191-198 (1985).

(56) References Cited

OTHER PUBLICATIONS

Paegel, et al., *Turn Geometry for Minimizing Band Broadening in Microfabricated Capillary Electrophoresis Channels*. Anal. Chem. 72: 3030-3037 (2000).

Blazej, R.G., et al., *Inline Injection Microdevice for Attomole-Scale Sanger DNA Sequencing*. Anal. Chem., 79(12): p. 4499-4506 (2007).

Scherer, et al. *High-Pressure Gel Loader for Capillary Array Electrophoresis Microchannel Plates*. BioTechniques 31: 1150-1156 (2001).

Koh, C.G., et al., *Integrating Polymerase Chain Reaction, Valving, and Electrophoresis in a Plastic Device for Bacterial Detection*. Anal. Chem., 75(17): 4591-4598 (2003).

Paegel, et al., *Microchip Bioprocessor for Integrated Nanovolume Sample Purification and DNA Sequencing*. Anal. Chem., 74: 5092-5098 (2002).

Blazej, et al. *Microfabricated Bioprocessor for Integrated Nanoliter-Scale Sanger DNA Sequencing*. Proc. Natl. Acad. Sci. USA 103: 7240-7245 (2006).

Olsen et al. *Immobilization of DNA Hydrogel Plugs in Microfluidic Channels*. Anal. Chem., 74: 1436-1441 (2002).

Ju, et al., *Fluorescence Energy-Transfer Dye-Labeled Primers for DNA—Sequencing and Analysis*. Proc. Natl. Acad. Sci. USA 92: 4347-4351 (1995).

Dressman et al., *Transforming Single DNA Molecules Into Fluorescent Magnetic Particles for Detection and Enumeration of Genetic Variations*. Proc. Natl. Acad. Sci. U.S.A., 100, (15), 8817-8822 (2003).

Margulies et al., *Genome Sequencing in Microfabricated High-density Picolitre Reactors*. Nature, doi:10.1038/nature 03959, 1-5 (2005).

Grover, et al., *Monolithic Membrane Valves and Diaphragm Pumps for Practical Large-Scale Integration Into Microfluidic Devices*. Sensors & Actuators B, 89: 315-323 (2003).

Grover, et al., *An Integrated Microfluidic Processor for Single Nucleotide Polymorphism-Based DNA Computing*. The Royal Society of Chemistry, Lab-on-a-Chip, 5: 1033-1040 (2005).

Amendment and Request for Correction of Inventorship mailed Jan. 10, 2008 in U.S. Appl. No. 10/750,533.

Anderson, et al. A miniature integrated device for automated multistep genetic assays. Nucleic Acids Research. 2000;28:e60.

Bings, et al. Microfluidic Devices Connected to Fused-Silica Capillaries with Minimal Dead Dead Volume. Analytical Chemistry. 1999;71(15):3292-3296.

Blazej, et al. Polymorphism Ratio Sequencing: A New Approach for Single Nucleotide Polymorphism Discovery and Genotyping. Genome Research. 2003;13:287-293.

Brenner, et al. Gene expression analysis by massively parallel signature sequencing (MPSS) on microbead arrays. Nature Biotechnology. 2000;18(6):630-634.

Buchholz, et al. The use of light scattering for precise characterization of polymers for DNA sequencing by capillary electrophoresis. Electrophoresis. 2001;22:4118-4128.

Caplus abstract of Krohkin et al. Modified silica as a stationary phase for ion chromatography. Journal of Chromatography A. 1995;706:93-8.

Chan, et al. Microfabricated Polymer Devices for Automated Sample Delivery of Peptides for Analysis by Electrospray Ionization Tandem Mass Spectrometry. Analytical Chemistry. 1999;71(20):4437-4444.

Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Curcio, et al. Continuous Segmented-Flow Polymerase Chain Reaction for High-Throughput Miniaturized DNA Amplification. Analytical Chemistry. 2003;75(1):1-7.

Diehl, et al. BEAMing: single-molecule PCR on microparticles in water-in-oil emulsions. Nature Methods. 2006;3(7):551-9.

Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.

Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.

Doyle, et al. Self-Assembled Magnetic Matrices for DNA Separation Chips. Science. 2000;295:2237.

Ewing, et al. Base-Calling of Automated Sequencer Traces Using Phred. I. Accuracy Assessment. Genome Research. 1998;8:175-185.

Ewing, et al. Base-Calling of Automated Sequencer Traces Using Phred. II. Error probabilities. Genome Research. 1998;8:186-194.

Figeys, et al. A Microfabricated Device for Rapid Protein Identification by Microelectrospray Ion Trap Mass Spectrometry. Analytical Chemistry. 1997;69(16):3153-3160.

Figeys, et al. An Integrated Microfluidics-Tandem Mass Spectrometry System for Automated Protein Analysis. Analytical Chemistry. 1998;70(18):3728-3734.

Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.

Figeys, et al. Nanoflow Solvent Gradient Delivery from a Microfabricated Device for Protein Identifications by Electrospray Ionization Mass Spectrometry. Analytical Chemistry. 1998;70(18):3721-3727.

Francis, et al. Flow analysis based on a pulsed flow of solution: theory, instrumentation and applications. Talanta. 2002;58(6): 1029-1042.

Ghadessy, et al. Directed evolution of polymerase function by compartmentalized self-replication. Proc Natl Acad Sci USA. 2001;98:4552-4557.

Giddings, et al. A software system for data analysis in automated DNA sequencing. Genome Research. 1998;8:644-665.

Goll, et al. Microvalves with bistable buckled polymer diaphragms. Journal of Micromechanics and Microengineering. 1996;6:77-79.

Grover, et al. Development and multiplexed control of latching pneumatic valves using microfluidic logical structures. Lab on a chip. 2006;6:623-631.

Grover, et al. Practical Valves and Pumps for Large-Scale Integration into Microfludic Analysis Devices. Micro Total Analysis Systems. 2002;1:136-138.

Hansen, et al. A robust and scalable microfluidic metering method that allows protein crystal growth by free interface diffusion. Proc Natl Acad Sci USA. 2002;99(26):16531-16536.

Harrison, et al. Micromachining a Miniaturized Capillary Electrophoresis-Based Chemical Analysis System on a Chip. Science 1993;261; 895-897.

Hayes, et al. Edge: A Centralized Resource for the Comparison, Analysis, and Distribution of Toxicogenomic Information. Molecular Pharmacology. 2005;67(4):1360-1368.

International Preliminary Report for corresponding PCT Application No. PCT/CA2000/01421 dated Feb. 14, 2002.

International Preliminary Report for corresponding PCT Application No. PCT/US2005/018678 dated Nov. 13, 2007.

International Preliminary Report for corresponding PCT Application No. PCT/US2005/033347 dated Mar. 20, 2007.

International Preliminary Report for corresponding PCT Application No. PCT/US2007/007381 dated Sep. 23, 2008.

International Preliminary Report for corresponding PCT Application No. PCT/US2007/02721 dated Aug. 5, 2008.

International Preliminary Report for corresponding PCT Application No. PCT/US2007/061573 dated Aug. 26, 2008.

International Search Report for PCT/US2005/033347.

Kan, et al. A novel thermogelling matrix for microchannel DNA sequencing based on poly-N-alkoxyalkylaclylamide copolymers. Electrophoresis. 2003;24(24):4161-4169.

Kopp, et al. Chemical Amplification Continuous-Flow PCR on a Chip. Science. 1998;280:1046-1048.

(56) References Cited

OTHER PUBLICATIONS

Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;B63(3):138-146.
Lagally, et al. Single-Molecule DNA Amplification and Analysis in an Integrated Microfluidic Device. Analytical Chemistry. 2001;73(3): 565-570.
Lazar, et al. Subattomole-Sensitivity Microchip Nanoelectrospray Source with Time-of-Flight Mass Spectrometry Detection. Analytical Chemistry. 1999;71(17):3627-3631.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole—time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Melin, et al. A Passive 2-Dimensional Liquid Sample Micromixer. 7th International Conference on Miniaturized Chemical and Biochemical Analysis Systems. 2003;167-170.
Mitra, et al. Digital genotyping and haplotyping with polymerase colonies. Proc Natl Acad Sci USA. 2003.100(10):15926-5931.
Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.
Ocvirk, ct al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.
Office Action Final dated Feb. 19, 2008 issued in U.S. Appl. No. 10/540,658.
Office Action Final dated Feb. 6, 2008 issued in U.S. Appl. No. 11/139,018.
Office Action mailed Apr. 27, 2007 in U.S. Appl. No. 11/139,018, filed May 25, 2005.
Office Action mailed Jul. 2, 2007 in U.S. Appl. No. 10/540,658, filed Jun. 23, 2005.
Office Action mailed Jul. 12, 2007 in U.S. Appl. No. 10/750,533, filed Dec. 29, 2003.
Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Paegel, et al. High-throughput DNA sequencing with a 96-lane capillary array electrophoresis bioprocessor. Proc Natl Acad Sci USA. 2002;99:574-579.
Paegel, et al. Microfluidic devices for DNA sequencing: sample preparation and electrophoretic analysis. Current Opinion in Biotechnology. 2003;14(1):42-50.
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.
Ramsey, et al. Generating Electrospray from Microchip Devices Using Electroosmotic Pumping. Analytical Chemistry. 1997;69(6):1174-1178.
Rohr, et al. Porous polymer monoliths: Simple and efficient mixers prepared by direct polymerization in the channels of microfluidic chips. Electrophoresis. 2001;22:3959-3967.
Rye, et al. High-sensitivity two-color detection of double-stranded DNA with a confocal fluorescence gel scanner using ethidium homodimer and thiazole orange. Nucleic Acids Research. 1991;19(2):327-333.
Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Takao, et al. A Pneumatically Actuated Full in-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Tice, et al. Formation of Droplets and Mixing in Multiphase Microfluidics at Low Values of the Reynolds and the Capillary Numbers. Langmuir. 2003;19:9127-9133.
Unger, et al. Monolithic Microfabricated Valves and Pumps by Multilayer Soft Lithography. Science. 2000;288:113-116.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Vazquez, et al. Electrophoretic Injection within Microdevices. Analytical Chemistry. 2002;74:1952-1961.
Veenstra, et al. The design of an in-plane compliance structure for microfluidical systems. Sensors and Actuators. 2002;B81:377-383.
Waller, et al. Quantitative Immunocapture PCR Assay for Detection of Campylobacter jejuni in Foods. Applied Environmental Microbiology. 2000.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
Wikipedia brochure for defining stocahstic process. Sep. 2, 2009.
Williams, et al. Amplification of complex gene libraries by emulsion PCR. Nature Methods. 2006;3(7):545-50.
Woolley, et al. Functional Integration of PCR Amplification and Capillary Electrophoresis in a Microfabricated DNA Analysis Device. Analytical Chemistry. 1996;68(23):4081-4086.

(56) References Cited

OTHER PUBLICATIONS

Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yang, et al. A MEMS thermopneumatic silicone rubber membrane valve. Sensors and Actuators. 1998;A64(1):101-108.
Yu, et al. Preparation of Monolithic Polymers with Controlled Porous Properties for Microfluidic Chip Applications Using Photoinitiated Free Radial Polymerization. Journal of Polymer Science. 2002;40:755-769.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.
Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
Zhang, et al. Microfabricated Devices for Capillary Electrophoresis-Electrospray Mass Spectrometry. Analytical Chemistry. 1999;71(15):3258-3264.
Chinese Office Action dated Jan. 25, 2008, from Application No. 2003801100666.
Hultman, T.S., et al. Bidirectional Solid-Phase Sequenceing of In Vitro-Amplified Plasmid DNA. Bio Techniques, 1991. 10:p. 84-93.
Nakano, H., et al., "Single-Step Single-Molecule PCR of DNA with a Homo-Priming Sequence Using a Single Primer and Hot-Startable DNA Polymerasem," Journal of Bioscience and Bioengineering, 2000, vol. 90:4, pp. 456-458.
Leamon, J.H., et al., A massively parallel Pico Titer Plate (TM) based platform for discrete picoliter-scale polymerase chain reactions, Electrophoresis, 2003, vol. 24, pp. 3769-3777.
Ghadessy, F.J., et al., "Directed evolution of polymerase function by compartmentalized self-replication," PNAS, 2001, vol. 98, pp. 4552-4557.
Fleming, et al., "LD-PCR coupled to long-read direct sequencing: an approach for mutation detection in genes with compact genomic structures," Journal of Biochemical and Biophysical Methods, 2001, vol. 47:1-2, pp. 131-136.
Kamei, T., et al., "Integrated Hydrogenated Amorphous Si Photodiode Detector for Microfluidic Bioanalytical Devices," Analytical Chemistry, 2003, vol. 75, pp. 5300-5305.
Albarghouthi, M.N., "Poly-N-hydroxyethylacrylamide (polyDuramide): A novel hydrophilic self-coating polymer matrix for DNA sequencing by capillary electrophroesis," Electrophoresis, 2002. vol. 23, pp. 1429-1440.
Song, H., et al., "A microfluidic system for controlling reaction networks in time," Angewandte Chemie-International Edition 42, 2003. pp. 768-772.
Srinivasan, U., et al., "Alkyltrichlorosilane-based self-assembled monolayer films for stiction reduction in silicon micromachines," Journal of Microelectromechanical Systems, 1998, vol. 7, pp. 252-260.
Thorsen et al., "Microfludic Large-Scale Integration", Science, vol. 298, Oct. 18, 2002, pp. 580-584.
Park, Nokyoung, et al., "Cylindrical Compact Thermal-Cycling Device for Continuous-Flow Polymerase Chain Reaction," Anal. Chem., Nov. 1, 2003, vol. 75, No. 21, pp. 6029-6033.
Emrich et al., "Microfabricated 384-lane capillary array electrophoresis bioanalyzer for ultrahigh-throughput genetic analysis," Analytical Chemistry, 2002, vol. 74:19, pp. 5076-5083.
Mathies, R.A., et al., "Capillary array electrophoresis bioprocessors, Solid-State Sensor," Actuator and Microsystems Workshop, 2002, pp. 112-117, Hilton Head Island, SC, USA.
Ligler, F.S., et al., "Integrating Waveguide Biosensor," Anal. Chem., 2002, vol. 74, pp. 713-719.
Notice of Allowance and Fees Due mailed Aug. 13, 2008 from U.S. Appl. No. 10/750,533.
Allowed Claims from U.S. Appl. No. 10/750,533.
Office Action dated Oct. 8, 2008 issued in U.S. Appl. No. 10/540,658.
Office Action Final dated Mar. 2, 2009 issued in U.S. Appl. No. 10/540,658.
International Search Report and the Written Opinion of the International Searching Report Oct. 29, 2007, Application No. PCT/US2005/018678.
Mathies, et al., U.S. Appl. No. 10/750,533, titled "Fluid Control Structures in Microfluidic Devices," filed Dec. 29, 2003.
Mathies, et al., U.S. Appl. No. 12/203,800, titled "Fluid Control Structures in Microfluidic Devices," filed Sep. 3, 2008.
Mathies, et al., U.S. Appl. No. 10/540,658, titled "Methods and Apparatus for Pathogen Detection and Analysis," filed Jun. 23, 2005.
Mathies, et al., U.S. Appl. No. 11/139,018, titled "Microfabricated Integrated DNA Analysis System," filed May 25, 2005.
Mathies, et al., U.S. Appl. No. 11/726,701, titled "Multiplexed Latching Valves for Microfluidic Devices and Processors," filed Mar. 21, 2007.
Office Action Final dated Aug. 27, 2008 issued in U.S. Appl. No. 11/139,018.
Office Action Final dated Apr. 29, 2009 issued in U.S. Appl. No. 11/139,018.
PCT Notification of Transmittal of the International Search Report and the Written Opinion of the International Searching Authority, or the Declaration, mailed Jul. 15, 2008, Application No. PCT/US2007/007381.
Iiidekuni, T., et al. Pneumatically Actuated Full in Channel Microvalve With MOSFET-Like Function in Fluid Channel Networks, Journal of Microelectromechanical Systems, 2002, 11:5; 421-426. P066).
Hidekuni, T., et al., Microfluidic Integrated Circuits for Signal Processing Using Analogous Relationship Between Pneumatic Microvalve and MOSFET, Journal of Microelectromechanical System 2003, 12:4; 497-505.
Mircea, C., et al., Design Fabrication and Testing of a Bistable Electromagnetically Actuated Microvalve. Journal of Microeclectromechanical System 2000. vol. 9; 181-189.
Press, W., et al., An Integrated Microfluidic Processor for Single Nucleotide Polymorphism-based DNA Computing, Lab on a Chip. 2005, 5:10, 8 pages.
Roth, C. et al., Fundamentals of Logic Design, $3^{rd}$ Edition, West Publishing Company, 1985 (Table of Content).
PCT Search Report mailed Oct. 29, 2007, Application No. PCT/US05/18678.
PCT Written Opinion mailed Oct. 29, 2007, Application No. PCT/US05/18678.
Press, W., et al., The Art of Scientific Computing, Numerical Recipes in C, 2nd Edition, Cambridge University Press, 1992, (table of Contents.
Office Action Final dated Dec. 11, 2009 issued in U.S. Appl. No. 11/726,701.
Office Action Final dated Nov. 6, 2009 issued in U.S. Appl. No. 11/139,018.
Office Action Final dated Feb. 22, 2010 issued in U.S. Appl. No. 11/139,018.
International Notification of Transmittal of the International Search Report and the Written Opinion mailed Jun. 17, 2008, Application No. PCT/US07/82568.
Notice of Allowance and Fees Due mailed May 6, 2010 from U.S. Appl. No. 11/726,701.
Allowed Claims from U.S. Appl. No. 11/726,701.
Chinese Office Action Final dated Feb. 24, 2010 issued Appl. No. 200780018073.1.

(56) References Cited

OTHER PUBLICATIONS

U.S. Appl. No. 12/026,510, filed Feb. 5, 2008, Jovanovich et al.
U.S. Appl. No. 12/820,390, filed Jun. 22, 2010, Harrison et al.
U.S. Appl. No. 12/845,650, filed Jul. 28, 2010, Jovanovich et al.
U.S. Appl. No. 12/949,623, filed Nov. 18, 2010, Kobrin et al.
Mathies, et al., U.S. Appl. No. 12/819,094, titled "Multiplexed Latching Valves for Microfluidic Devices and Processors," filed Jun. 18, 2010.
Japanese Office Action mailed Mar. 1, 2011 for Appln. No. 2007-515379.
European Office Action mailed Apr. 7, 2011 from Application No. 05804847.1
Coleman, et al. A sequential injection microfluidic mixing strategy. Microfluidics and Nanofluidics. 2005;319-327.
Ericson, et al. Electroosmosis- and Pressure-Driven Chromatography in Chips Using Continuous Beds. Analytical Chemistry. 2000;72(1):81-87.
International search report and written opinion dated Mar. 24, 2011 for PCT Application No. US2010/58227.
International search report and written opinion dated Sep. 1, 2010 for PCT Application No. US2010/040490.
International search report dated Oct. 6, 2010 for PCT Application No. US10/37545.
International search report dated Apr. 5, 2001 for PCT Application No. CA2000/01421.
International search report dated May 14, 2010 for PCT Application No. US2009/06640.
International search report dated Jul. 11, 2008 for PCT Application No. US07/61573.
International search report dated Jul. 30, 2010 for PCT Application No. US2010/36464.
International search report dated Aug. 18, 2009 for PCT Application No. US09/00419.
International search report dated Aug. 26, 2004 PCT Application No. US2003/41466.
International search report dated Sep. 25, 2007 for PCT Application No. US2007/02721.
International Search Report for PCT/US2005/033347—Annex to Form PCT/ISA/206.
Jacobson, et al. Electrokinetic Focusing in Microfabricated Channel Structures. Anal. Chem., 1997, 69 (16), pp. 3212-3217.
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
MillGat pump user manual, version 2.12, published 2005, pp. 1-28.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.
Mathies, et al., U.S. Appl. No. 12/670,377, titled "Microfabricated Droplet Generator for Single Molecule/Cell Genetic Analysis in Engineered Monodispersed Emulsions," filed Jan. 22, 2010.
European Supplemental International Search Report dated Dec. 18, 2009 PCT Application No.
Kamel, T., et al., "Integrated Hydrogenated Amorphous Si Photodiode Detector for Microfluidic Bioanalytical Devices," Analytical Chemistry, 2003, vol. 75, pp. 5300-5305.
Koch, et al. "Optical flow cell multichannel immunosensor for the detection of biological warefare agents" Biosensors & Bioelectrics 14 (2000) pp. 779-784.
Yacoub-George, et al. "Chemiluminescence multichannel immunosensor for biodetection" Analytica Chimica Acta 457 (2002) pp. 3-12.
Delehanty, et al. "A Microarray Immunoassay for Simultaneous Detection of Proteins and Bacteria" Anal. Chem. 2002, 74, pp. 5681-5687.
Rowe-Taitt, et al., "Simultaneous detection of six biohazardous agents using a planar waveguide array biosensor", Biosensors & Bioelectronics 15 (2000) pp. 5798-589.
Rowe, et al., "Array Biosensor for Simultaneous Identification of Bacterial, Viral and Protein Analytes" Anal. Chem. 1999, 71 pp. 3846-3852.
O'Mahony, et al. "A real time PCR assay for the detection and quantitation of Mycobacterium avium subsp. Paratuberculosis using SYBR Green and the Light Cycler" Journal of Microbiological Methods 51 (2002) pp. 283-293.
Papadelli, et al., "Rapid detection and identification of *Streptococcus macedonicus* by species-specific PCR and DNA hybridisation" International Journal of Food Microbiology 81 (2003) pp. 231-239.
Hansen, et al. "Polymerase chain reaction assay for the detection of *Bacillus cereus* group cells" FEMS Microbology Letters 202 (2001) pp. 209-213.
Kong, et al. "Rapid detection of six types of bacterial pathogens in marine waters by multiplex PCR" Walter Research 36 (2002) pp. 2802-2812.
Nataro, et al. "Diarrheagenic *Escherichia coli*" Clinical MicroBiology Reviews, Jan. 1998 pp. 142-201.
Kimura, et al. Restriction-Site-Specific PCR as a Rapid Test to Detect Enterohemorrhagic *Escherichia coli* O157:H7 Strains in Environmental Samples; Applied and Environmental Microbiology Jun. 2000 (pp. 2513-2519).
Peng, et al. "Immuno-capture PCR for detection of *Aeromonas hydrophila*" Journal of Microbiological Methods 49 (2002) pp. 335-338.
Call, et al. "Detecting and genotyping *Escherichia coli* O157:H7 using multiplexed PCR and nucleic acid microarrays" International Journal of Food Microbiology 67 (2001) pp. 71-80.
White, et al., "Flash detection/identification of pathogens, bacterial spores and bioterrorism agent biomarker from clinical and environmental matrices" Journal of Microbiological Methods 48 (2002) pp. 139-147.
Ruan, et al. "Immunobiosensor Chips for Detection of *Escherichia coli* O157:H7 Using Electrochemical Impedance Spectroscopy" Anal. Chem 2002 74 pp. 4814-4820.
Gau, et al., "A MEMS based amperometric detector for *E. coli* bacteria using self-assembled monolayers" Biosensors & Bioelectronics 16 (2001) pp. 745-755.
Kourentzi, et al., "Microbial identification by immunohybridization assay of artificial RNA labels" Journal of Microbiological Methods 49 (2002) pp. 301-306.
Belgrader, et al. "Rapid PCR for Identity Testing Using a Battery-Powered Miniature Thermal Cycler" J Forensic Sci. 1998, pp. 315-319.
Belgrader, et al. "A Minisonicator to Rapidly Disrupt Bacterial Spores for DNA Analysis" Anal. Chem 1999 pp. 4232-4236.
Belgrader, et al. "PCR Detection of Bacteria in Seven Minutes" Science Magazine vol. 284, Issue 5413 (1999) pp. 449-450.
Verlee, et al. "Fluid Circuit Technology: Integrated Interconnect Technology for Miniature Fluidic Devices" Abbott Laboratories Hospital Division, Abbott Park, IL (1996) pp. 9-14.
Dodson, et al., "Fluidics Cube for Biosensor Miniaturization" Anal. Chem 2001 pp. 3776-3780.
Walt, et al., "Biological Warefare" Analytical Chemistry (2000) pp. 739-746.
Yang, et al. "An Integrated Stacked Microlaboratory for Biological Agent Detection with DNA and Immunoassays" Biosensors & Bioelectronics 17 (2002) pp. 605-618.
Reyes, et al. "Micro Total Analysis Systems. 1. Introduction Theory and Technology" Anal Chem (2002) pp. 2623-2636.
Auroux, et al. "Micro Total Analysis Systems 2. Analytical Standard Operations and Applications" Anal. Chem 2002 pp. 2637-2652.
Manz, et al. "Miniaturized Total Chemical Analysis Systems: A Novel Concept for Chemical Sensing" Sensors & Actuators (1990) pp. 244-248.
Jacobson, et al. "High-Speed Separations on a Microchip" Anal. Chem 1994 pp. 1114-1118.
Soper, et al. "Polymeric Microelectro-mechanical Systems" Anal. Chem (2000) pp. 643-651.

(56) References Cited

OTHER PUBLICATIONS

Shi, et al. "Radial Capillary Array Electrophoresis Microplate and Scanner for High Performance Nucleic Acid Analysis" Anal. Chem 1999 pp. 5354-5361.
Waters, et al. "Microchip Device for Cell Lysis, Multiplex PCR Amplification, and Electrophoretic Sizing" Anal. Chem 1999 pp. 158-162.
Jacobson, et al. "Integrated Microdevice for DNA Restriction Fragment Analysis" Anal. Chem 1996 pp. 720-723.
Burns, et al. "An Integrated Nanoliter DBA Analysis Device" Science Magazine 1998 pp. 484-487.
Duffy, et al. "Rapid Prototyping of Microfluidic Systems in Poly(dimethylsiloxane)" Anal. Chem 1998 (pp. 4974-4984.
Quake, et al. "From Micro-to Nanofabrication with Soft Materials" Science Magazine (2000) pp. 1536-1540.
Medintz, et al. "High-Performance Genetic Analysis Using Microfabricated Capillary Array Electroporesis Microplates" Electrophoresis 2001 pp. 3845-3856.
Medintz, et al. "High-Performance Multiplex SNP Analysis of Three Iiemochmromatosis-Related Mutations with Capillary Array Electrophoresis Microplates" Genome Research 2001 pp. 413-421.
Medintz, et al. "Genotyping Energy-Transfer Cassette Labeled Short Tandem Repeat Amplicons with Capillary Array Electrophoresis Microchannel Plates" Clinical Chemistry (2001) pp. 1614-1621.
Webster, et al. "Monolithic Capillary Electrophoresis Device with Integrated Fluorescence Detector" Anal. Chem 2001 pp. 1622-1626.
Kamel, et al. "Integrated Amorphous Silicon Photodiode Detector for Microfabricated Capillary Electrophoresis Devices" Micro Total Analysis Systems 2002 pp. 257-259.
Kuhnert, et al. "Detection System for *Escherichia coli*-Specific Virulence Genes: Absence of Virulence Determinants in B and C Strains" applied and Environmental Microbiology (1997) pp. 703-709.
Stumpfle, et al. "Absence of DNA sequence homology with genes of the Excherichia coli hemB locus in Shiga-toxin producing *E. coli* (STEC) 0157 Strains" FEMS Microbiology Letters 174 (1999) pp. 97-103.
Chandler, et al. "Automated immunomagnetic separation and microarray detection of *E. coli* 0157:H7 from poultry carcass rinse" International Journal of Food Microbiology 70 (2001) pp. 143-154.
Tian, et al. "Evaluation of Silica Resins for Direct and Efficient Extraction of DNA from Complex Biological Matrices in a Miniaturized Format" Analytical Biochemistry 283 (2000) pp. 175-191.
Cameron, et al. "High Internal Phase Emulsions (HIPEs) Structure, Properties and Use in Polymer Preparation" University of Strathclyde pp. 163-214.
He, et al. "Fabrication of Nanocolumns for Liquid Chromatography" Anal. Chem 1998 pp. 3790-3797.
Birnmoim, H.C. "A Rapid Alkaline Extraction Method for the Isolation of Plasmid DNA" Methods of Enzymology vol. 100 (1983) pp. 243-255.
McLaughlin, et al. "Molecular Approaches to the Identification of Streptococci" Methods in Molecular Medicine vol. 15 pp. 117-139.
Zhu, et al., "High-Sensitivity Capillary Electrophoresis of Double-Stranded DNA Fragments Using Monomeric and Dimeric Fluorescent Intercalating Dyes" Anal Chem 1994 pp. 1941-1948.
Medintz, et al. "Novel Energy Transfer Fluorescence Labeling Cassette" BioTechniques vol. 32 No. 2 (2002) p. 270.
Sun, et al. "A Heater-Integrated Transparent Microchannel Chip for Continuous Flow PCR" Sensors and Actuators B 84 (2002) pp. 283-289.
PCT International Search Report dated Aug. 26, 2004, Application No. PCT/US03/41466.
Canadian Office Action dated Jun. 10, 2011, Application No. 2,512,071.
Notification of Provisional Rejeciton mailed Oct. 21, 2011 for Application No. 2006-7026091.
Final Office Action mailed Sep. 12, 2011 from U.S. Appl. No. 12/844,544.
Koren Office Action mailed Oct. 11, 2011, in Application No. 2005-7012095.
Chinese Office Action mailed Oct. 9, 2011, in Application No. 200910160476.0.
Chinese Notice of Amendment issued Aug. 30, 2011 for Appl. No. 201110197721.2.
Office Action Final dated Feb. 8, 2012 issued in U.S. Appl. No. 12/203,800.
Korean Office Action mailed Oct. 11, 2011, for Application No. 2011-7015771.
Office Action Final dated Feb. 24, 2012 issued in U.S. Appl. No. 12/819,094.
Office Action dated Apr. 12, 2012 issued in U.S. Appl. No. 13/372,376.
Notice of Allowance mailed Jun. 8, 2012 for U.S. Appl. No. 12/819,094.
Allowed Claims as of Jun. 8, 2012 for U.S. Appl. No. 12/819,094.
Office Action dated Jul. 6, 2012 issued in U.S. Appl. No. 12/670,377.
Final Office Action dated Jul. 13, 2012 issued in U.S. Appl. No. 12/203,800.
Japanese Office Action mailed Sep. 4, 2012 for Application No. 2011-155300.
Japanese Decision on Rejection mailed Apr. 3, 2012 for Application No. 2007-515379.
European Office Action mailed Oct. 23, 2012 from Application No. 05804847.1
Japanese Decision of Rejection dated Mar. 15, 2011, from Application No. 2005-508628.
International Search Report mailed Oct. 10, 2008 issued in PCT/US2008/071086.
Notice of Allowance dated Dec. 10, 2012 issued in U.S. Appl. No. 13/372,376.
Office Action dated Nov. 4, 2013 issued in U.S. Appl. No. 11/978,224.
Office Action dated Feb. 27, 2014 issued in U.S. Appl. No. 12/203,800.
Mathies, et al., U.S. Appl. No. 12/844,544, titled "Microfabricated Integrated DNA Analysis System," filed Jul. 27, 2010.
Japanese Office Action dated Jan. 13, 2010, from Application No. 2005-508628.
Japanese Office Action dated Aug. 10, 2010, from Application No. 2005-508628.
European Supplemental Search Report dated Sep. 1, 2010 from Application No. 05804847.1
Mathies, et al., U.S. Appl. No. 12/782,598, titled "Fluid Control Structures in Microfluidic Devices," filed May 18, 2010.
Hartmann, A., et al., "Direct immobilization of Antibodies on Phthalocyaninato-polysiloxane Photopolymers," Thin Solid Films, 245, 1994, pp. 206-210.
Hartmann, A., et al., One-Step Immobilization of Immunoglobulin G and Potential of the Method for Application in Immunosensors, Sensors and Actuators 28 (2), 1995, pp. 143-149.
Sanford, et al., "Photoactivatable Cross-Linked Polyacrylamide for the Site-Selective Immobilization of Antigens and Antibodies," Chem Mater., 1998, vol. 10, No. 6, pp. 1510-1520.
Office Action mailed Jan. 7, 2011 from U.S. Appl. No. 12/844,544.
Notification of Provisional Rejection received Jan. 17, 2011, in Application No. 2005-7012095.
Yu, Cong, et al., "Towards Stationary Phases for Chromatography on a Microchip: Molded Porous Polymer Monoliths Prepared in Capillaries by Photoinitiated in situ Polymerization as Separation Media for Electrochromatography," Electrophoresis 2000, vol. 21, pp. 120-127.
Request for Ex Parte Reexamination of U.S. Patent No. 7,445,926.
Hosokawa, et al., "A Pneumatically-Actuated Three-Way Microvalve Fabricated with Polydimethylsiloxane Using the Membrane Transfer Technique," J. Micrmech. Microeng., vol. 10, 2000, pp. 415-420.

\* cited by examiner

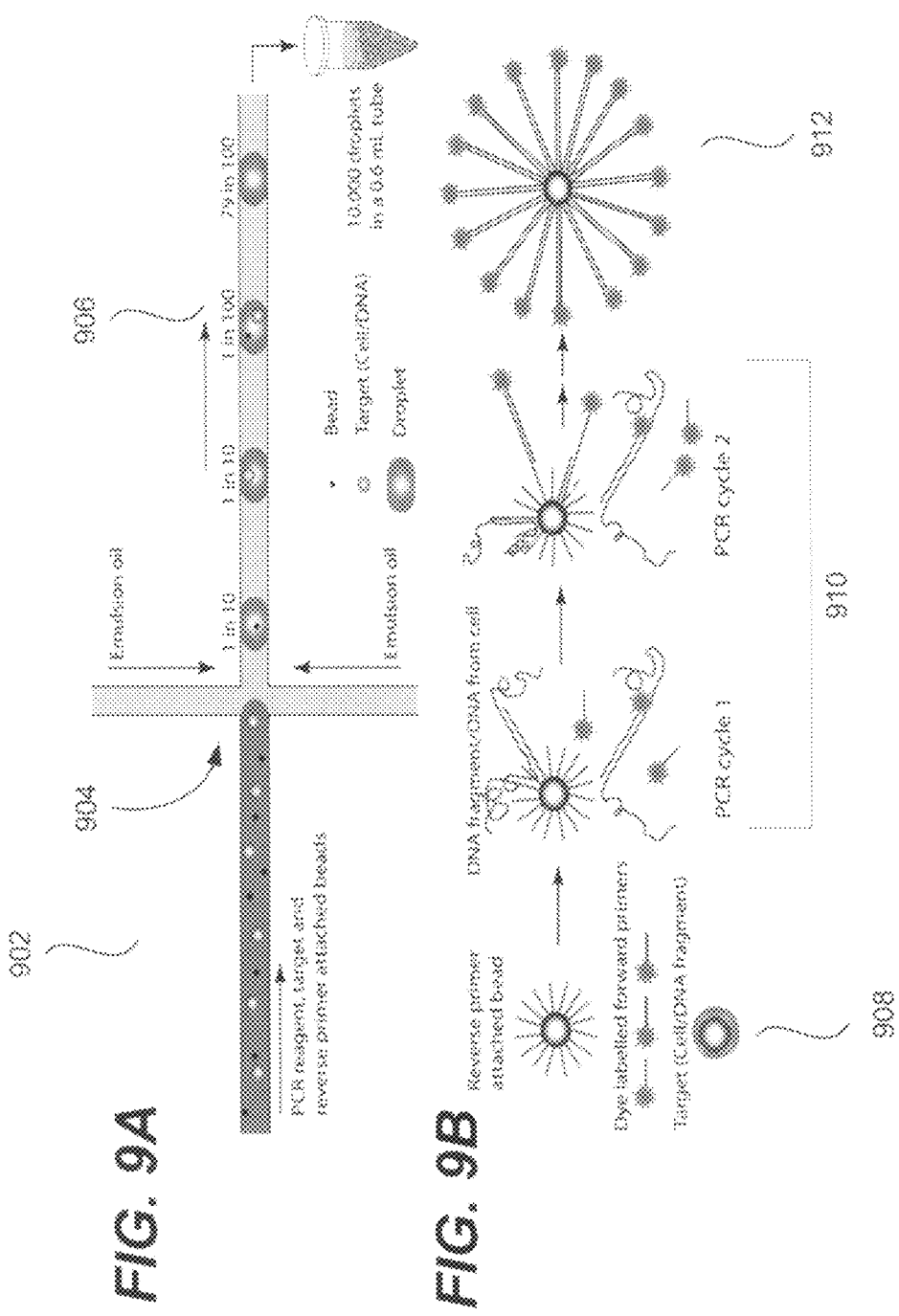

```
                        SEQUENCE LISTING

<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: amplification primer

<400> SEQUENCE: 1
aagcctaaat agcccacacg ttcc                                            24

<210> SEQ ID NO 2
<211> LENGTH: 24
<212> TYPE: DNA
<213> ORGANISM: Artificial
<220> FEATURE:
<223> OTHER INFORMATION: amplification primer

<400> SEQUENCE: 2
tggttaggct ggtgttaggg ttct                                            24

<210> SEQ ID NO 3
<211> LENGTH: 18
<212> TYPE: DNA
<213> ORGANISM: Artificial
<220> FEATURE:
<223> OTHER INFORMATION: standard primer

<400> SEQUENCE: 3
gttttcccag tcacgacg                                                   18

<210> SEQ ID NO 4
<211> LENGTH: 20
<212> TYPE: DNA
<213> ORGANISM: Artificial
<220> FEATURE:
<223> OTHER INFORMATION: affinity capture oligonucleotide

<400> SEQUENCE: 4
agacctgtga tccatcgtga                                                 20
```

INLINE-INJECTION MICRODEVICE AND MICROFABRICATED INTEGRATED DNA ANALYSIS SYSTEM USING SAME

CROSS REFERENCE TO RELATED APPLICATIONS

This application claims priority under 35 U.S.C. 119(e) from Provisional U.S. Patent Application Ser. No. 60/854,570, filed Oct. 25, 2006, entitled "INLINE-INJECTION MICRODEVICE FOR ATTOMOLE-SCALE SANGER DNA SEQUENCING," and from Provisional U.S. Patent Application Ser. No. 60/881,411, filed Jan. 19, 2007, entitled "MICROBEAD-BASED SANGER SEQUENCING," which are incorporated herein by reference in their entireties.

STATEMENT REGARDING FEDERALLY SPONSORED RESEARCH

This invention was made with United States government support under Grant Number HG003583 awarded by the National Institute of Health. The United States government has certain rights in this invention.

BACKGROUND

1. Field of Invention

The present invention relates to microfabricated and microfluidic structures. In one example, the present invention relates to a microfabricated system and method for genome sequencing.

2. Description of Related Art

The cross-injector is utilized in nearly all academic and commercial microfabricated capillary electrophoresis (µCE) applications to form small, well-defined sample plugs. FIG. 1 shows a simple schematic of a cross-injection system used in microdevices. In FIG. 1, injection channel 109 is connected to sample reservoir 101 and sample waste reservoir 103. Separation channel 111 has buffer inlet reservoir 105 and buffer outlet reservoir 107. Electrodes are associated with reservoirs 101, 103, 105 and 107. In operation, a sample containing an unpurified analyte, e.g., DNA, is placed in the sample reservoir 101 and an electric potential is applied between the sample reservoir 101 and the waste reservoir 103. A sample is drawn from the sample reservoir 101 across the injection channel 109. By controlling the voltage across the injection and separation channels, a sample plug can be formed at the intersection 113 of the channels. The sample plug is then injected into the separation channel 111 by applying a potential across the separation channel, between reservoirs 105 and 107. In this manner, a sample is injected into the separation channel. Using the cross-injector, however, an excess sample volume is necessary to form and inject the sample plug. In addition, without desalting, the sample plug will contain ionic buffer and other ionic reagents. Because of these factors, cross-injector systems have efficiencies of 1% or less.

In advanced integrated microdevice systems that seek to miniaturize not only CE but all processing steps, the cross-injector is a barrier to reaching theoretical miniaturization limits. Additionally, cross-injection timing requirements can hinder optimization of array CE microdevices and integrated bioprocessor systems operating on limiting amounts of template. T-injection designs also present requirements that have similar barriers to miniaturization and timing optimization. Direct analyte injection that has been used in certain CE applications yields low-resolution, low-sensitivity separations due to the large sample plug size and injection of contaminants that are not suitable for applications such as Sanger DNA sequencing.

SUMMARY

Methods and microfluidic circuitry for inline injection of nucleic acids for capillary electrophoresis analysis are provided. According to various embodiments, microfabricated structures including affinity-based capture matrixes inline with separation channels are provided. The affinity-based capture matrices provide inline sample plug formation and injection into a capillary electrophoresis channel. Also provided are methods and apparatus for microbead-based inline injection system for a DNA sequencing.

In one aspect, the invention features a microfabricated structure for inline injection of a sample plug into a separation channel. The structure includes a sample channel region for containing an unpurified sample of an analyte; a capture channel region containing a capture matrix for forming a concentrated sample plug, wherein the capture matrix has a selective affinity for the analyte; and a separation channel region to receive the sample plug and separate the analyte, wherein the capture channel and separation channel regions are contiguous and/or arranged in a line.

In another aspect, the invention features a microfabricated structure for inline injection of a sample plug into a separation channel. The structure includes a sample region means for containing an unpurified sample of an analyte; a capture matrix means for forming a concentrated sample plug; means for inline injecting the sample plug into a separation channel; and the separation channel means for receiving the sample plug and separating the analyte.

In another aspect the invention features a radial array of inline injection and separation elements. Each element includes a sample channel region for containing an unpurified sample of an analyte; a capture channel region containing a capture matrix for forming a concentrated sample plug, wherein said capture matrix has a selective affinity for the analyte; a separation channel region to receive the sample plug and separate the analyte, wherein the capture and separation channel regions are contiguous and/or are arranged in a line; a reagent distribution channel linking the sample channel regions; a capture matrix distribution channel linking the capture channel regions; and an anode common to all elements.

In yet another aspect, the invention features a microfabricated structure for paired-end sequencing. The structure includes a plurality of sequencing elements. Each element includes a thermal cycling reactor for producing forward and reverse extension fragments from a sequencing template; a forward capture channel region containing a forward capture matrix for concentrating forward extension fragments, wherein said forward capture matrix supports an oligonucleotide that selectively hybridizes to the forward extension fragments; a reverse capture channel region containing a reverse capture matrix for concentrating reverse extension fragments, wherein said reverse capture matrix supports an oligonucleotide that selectively hybridizes to the reverse extension fragments; a forward separation channel to separate the forward extension fragments, wherein the forward capture channel region and the forward separation channel region are contiguous and/or arranged in a line; and a reverse separation channel to separate the reverse extension fragments, wherein the reverse capture channel region and the reverse separation channel region are contiguous and/or arranged in a line.

Certain implementations of the structure for paired-end sequencing include a forward capture matrix distribution channel to distribute forward capture matrix material into the forward capture channel region and/or a reverse capture matrix distribution channel to distribute reverse capture matrix material into the reverse capture channel region. Certain implementations also include a transfer channel connecting the forward and reverse capture channel regions.

Another aspect of the invention features a microfabricated structure including a distribution channel configured to distribute microreactor elements carrying multiple copies of a clonal sequencing template into each of a plurality of channels such that only one microreactor element will pass into one channel, wherein each channel comprises a thermal cycling chamber connected to a purification chamber connected to a component separation channel, wherein thermal cycling extension fragments are produced from a microreactor element in the thermal cycling chambers; the purification chambers are configured to capture and concentrate the extension fragments; and the component separation are configured to analyze the extension fragments, and further wherein each component separation channel is contiguous with and/or is arranged in a line with a purification chamber and configured to receive the concentrated extension fragments via inline injection from that purification chamber.

Another aspect of the invention features a device including a channel defining a flow path between a first end and a second. The channel includes a capture channel region containing an affinity capture matrix and a separation channel region, wherein the capture channel region and the separation channel regions are contiguous and/or arranged in a line. The device may also include a first electrode in electrical communication with a first end of the channel; a waste port in fluid communication with the capture channel region; a second electrode in electrical communication with the waste port, wherein a voltage applied between the first and second electrodes moves charged molecules through the capture channel region to the waste port; and a third electrode in electrical communication with a second end of the sample channel, wherein a voltage applied between the first and third electrodes moves charged molecules from the capture channel region through the separation channel region.

A further aspect of the invention features a system for performing sequencing. The system may include means for shearing DNA into DNA fragments; means for ligating the DNA fragments to form a mixture of desired circular and contaminating linear products; means for exonuclease degradation for selectively removing the contaminating linear products; emulsion PCR reaction means for generating microspheres carrying multiple clonal copies of a single DNA sequencing template; fluorescent activated cell sorting (FACS) means for selecting which microspheres have a DNA sequencing template; microfluidic distribution channel means for distributing a selected microsphere with a DNA sequencing template into a thermal cycling chamber; valving means for ensuring that statistically only one microsphere will flow into one thermal cycling chamber; Sanger extension means, including the thermal cycling chambers, for producing thermal cycling extension fragments from the microspheres carrying multiple copies of the DNA sequencing template; capture means for capturing, purifying and concentrating the extension fragments into a sample plug; means for releasing the sample plug from the capture means; means for inline injecting the sample plug into a capillary array electrophoresis channel; and separation means, including a capillary array electrophoresis channel, for analyzing the extension fragments.

Implementations of the invention may also include one or more of the following features: a reagent distribution channel to distribute microreactor elements carrying multiple copies of a clonal sequencing template into a plurality of thermal cycling chambers, wherein each thermal cycling chamber receives exactly one unique clonal sequencing template; passive or active valving to distribute the microreactor elements into the plurality of thermal cycling chambers, a waste port located downstream of the capture channel region and upstream of the separation channel region, a cathode upstream of the capture channel region and an anode downstream of the separation channel region, Implementations of the invention may also feature one or more of: a capture matrix that contains least one of a gel, including a UV-polymerized gel, immobilized beads, a porous monolith, dense posts, pillars and weirs, a capture matrix that supports a capture compound having a selective affinity for the analyte, and a capture matrix that forms a purified and concentrated sample plug. In certain implementations, the sample channel region includes a thermal cycler chamber to produce extension fragments from a sequencing template. Also in certain implementations, the analyte comprises extension fragments from a DNA or RNA template and the capture matrix supports an oligonucleotide complementary to a portion of the extension fragments. Certain implementations feature a sample channel region having volume between about 110-1000 nanoliters and/or a capture channel region having a volume between about 1-1000 nanoliters, for example, 1-100 nanoliters.

Another aspect of the invention features a process of introducing an analyte in a sample to a separation channel. The process includes the operations of introducing a sample containing an analyte to a sample channel region; driving the analyte in the sample to a capture channel region containing a capture matrix, said matrix having a selective affinity for the analyte; forming a concentrated sample plug in the capture channel region; and inline injecting the concentrated sample plug from the capture channel region into the separation channel.

Yet another aspect of the invention features a process for performing sequencing including the operations of distributing microreactor elements with DNA sequencing templates into thermal cycling chambers, wherein each microreactor element has multiple clonal copies of a single unique sequencing template; producing thermal cycling extension fragments from the microreactor elements carrying multiple copies of a sequencing template; forming a concentrated sample plug of the extension fragments in a capture channel region comprising a capture matrix; inline injecting the sample plug from the capture matrix into a separation channel; and separating the extension fragments in the separation channel.

Another aspect of the invention features a process for performing sequencing that includes the operations of distributing microreactor elements with DNA sequencing templates into thermal cycling chambers, wherein each microreactor element has multiple clonal copies of a single unique sequencing template; producing thermal cycling extension fragments from the microreactor elements carrying multiple copies of a sequencing template; forming a concentrated sample plug of the extension fragments in a capture channel region comprising a capture matrix; injecting the sample plug from the capture matrix into a separation channel, wherein at least about 50% of the extension fragments produced are injected into the separation channel. In certain implementations at least 70%, 80%, 90% or substantially all of the extension fragments produced are injected into the separation channel.

Another aspect of the invention features a method that includes the operations of providing in a sample port a sample comprising analyte molecules and non-analyte molecules; moving the sample to a sample channel region; applying an electrical potential across a fluid path comprising the sample channel region, a capture channel region and a waste port, wherein the capture channel region comprises an affinity capture matrix configured to capture analyte molecules and wherein non-analyte molecules are moved by the electrical potential to the waste port; releasing captured analyte molecules from the affinity capture matrix; applying an electrical potential across a second fluid path comprising the capture channel region and a separation channel region of a separation channel, wherein the separation channel region is contiguous with and/or arranged in a line with the capture channel and wherein analyte molecules are moved by the electrical potential through the separation channel, whereby analyte molecules are resolved; and detecting the resolved analyte molecules in the separation channel.

Certain implementations of the invention may further include one or more of forming a purified sample plug in the capture channel region, forming extension fragments from a sequencing template in the thermal cycling reactor, forming a concentrated sample plug in the capture channel region by selective hybridizing of at least some of the extension fragments to oligonucleotides in the capture matrix, thermally releasing the sample plug from the capture matrix prior to injection, applying an electric potential across the capture matrix to inline inject the sample, introducing capture matrix material into the capture channel region and photo-polymerizing at least a portion of the capture matrix material to produce the capture matrix. Also in certain implementations, the reagent distribution is done such that only one microreactor element will pass into one thermal cycling chamber.

In certain implementations, a microreactor element including a microcarrier element which carries the multiple copies of a clonal sequencing template, is used. The microreactor element may be a bolus or a microemulsion droplet and the microreactor element a microbead carrying the multiple copies of the clonal sequencing template.

BRIEF DESCRIPTION OF DRAWINGS

The invention may best be understood by reference to the following description taken in conjunction with the accompanying drawings that illustrate specific embodiments of the present invention.

FIGS. 9A and 9B are diagrammatic representations of a process of producing nanoliter emulsion particles in accordance with embodiments of the invention.

DETAILED DESCRIPTION

Reference will now be made in detail to some specific embodiments of the present invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. The present invention may be practiced without some or all of these specific details. In other instances, well known process operations have not been described in detail in order not to unnecessarily obscure the present invention.

Furthermore, techniques and mechanisms of the present invention will sometimes be described in singular form for clarity. However, it should be noted that some embodiments can include multiple iterations of a technique or multiple applications of a mechanism unless noted otherwise.

The devices, systems and methods of the present invention will be described in connection with DNA sequencing. In particular the devices, systems and methods are described in the context of capillary gel electrophoresis of DNA. However, the system and method may also be used for RNA sequencing. Additionally, the system and method may be used for other genetic analysis of DNA or RNA, as well as for microchip-based inline injection of other analytes into separation or analysis channels.

The devices and methods for microchip electrophoresis use serial domains of nanoliter-scale sample containment, affinity-based sample plug formation and separation material for inline purification, preconcentration and injection of samples. The affinity-based sample plug formation occurs in a capture channel region that contains a capture matrix that has a selective affinity for the analyte. In many embodiments, the capture matrix includes a capture compound supported by a gel or bead matrix. For example, an unpurified sequencing sample is electrophoretically driven into a capture channel region containing an oligonucleotide capture probe that simultaneously performs sample clean-up and defined, ready-to-inject sample plug formation. The plug is directly injected into the CE channel by direct application of the separation voltage after raising the temperature to release the captured and purified product. This eliminates the need for the excess sample or delicate timing sequence that is required for cross-injection.

Figure 1:
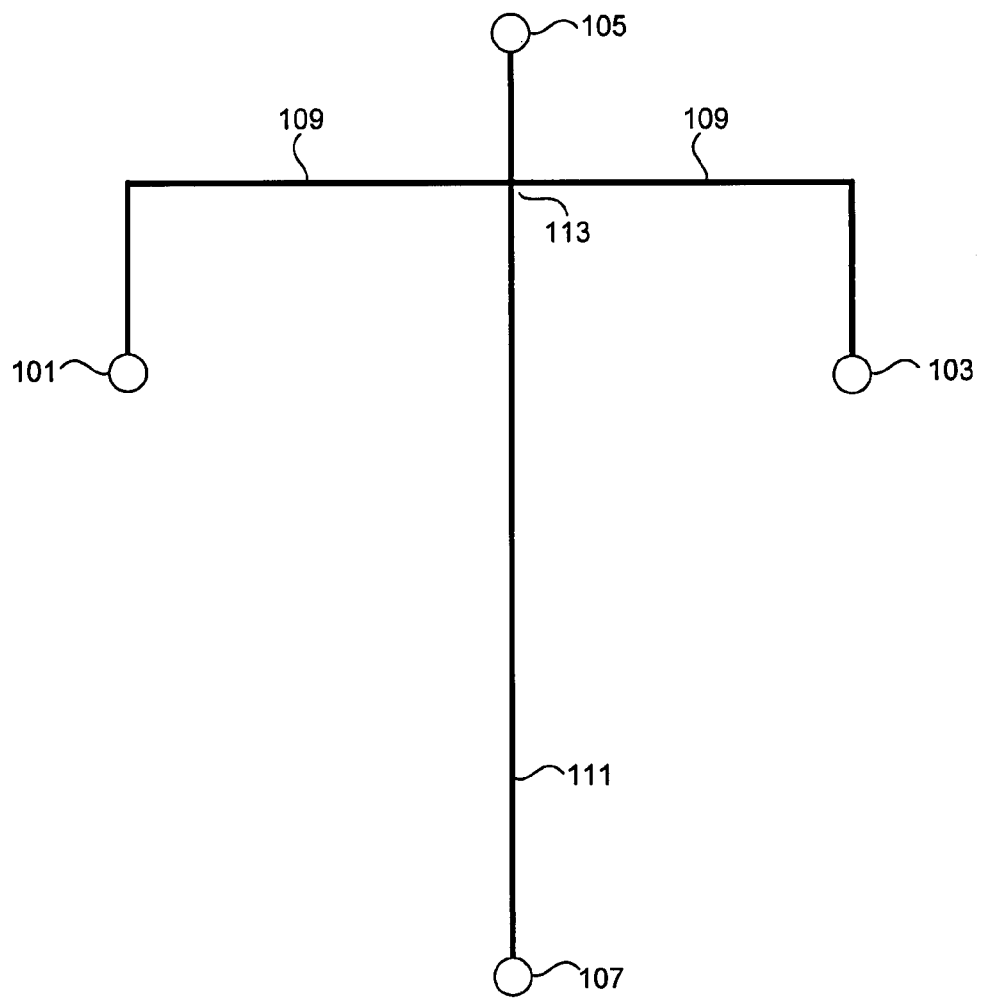
FIG. 1 is a diagrammatic representation of a cross-injector used in a conventional microdevice.
Figure 2A:
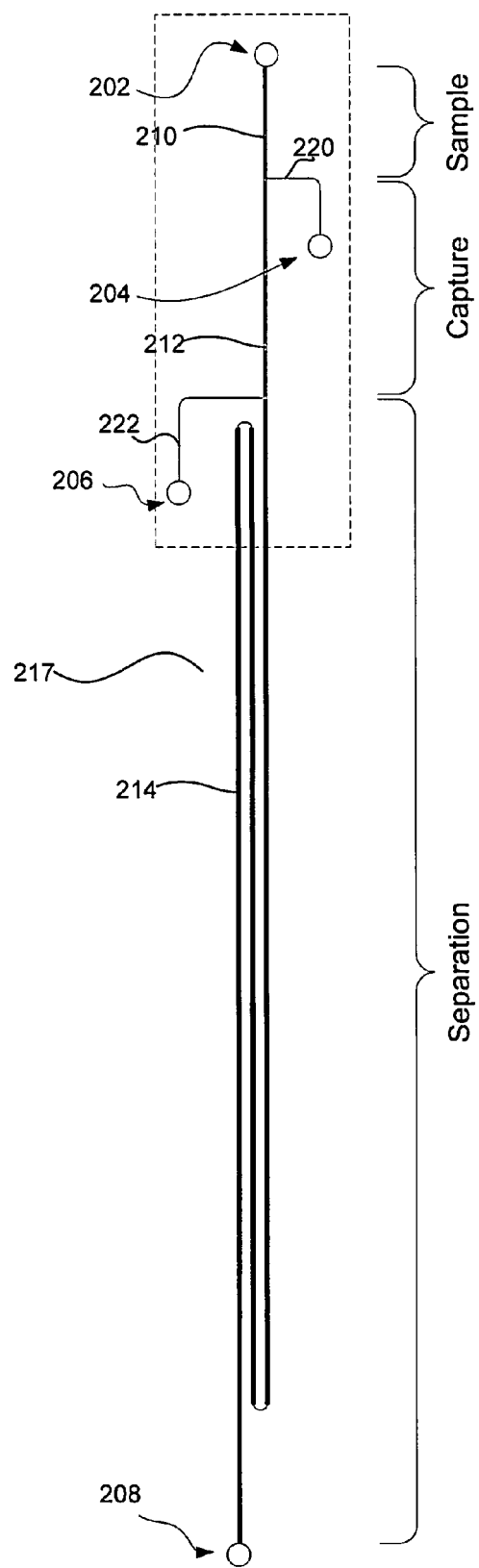
FIG. 2A is a diagrammatic representation of an inline injection system in accordance with embodiments of the invention.
Figure 2B:
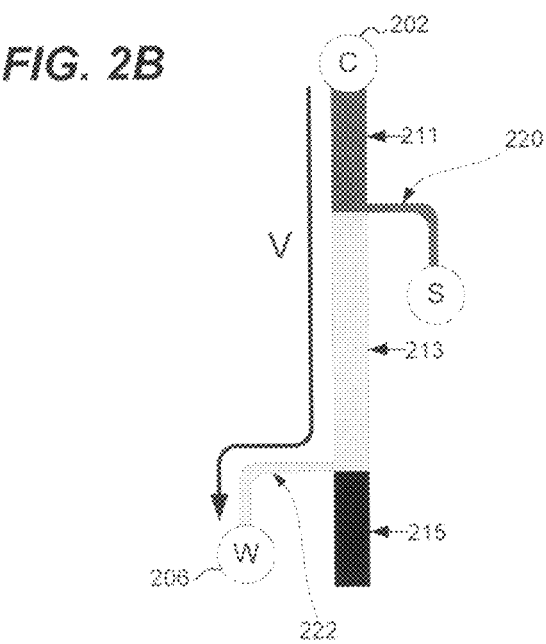
FIGS. 2B-2E are diagrammatic representation of steps involved in an inline injection and separation process in accordance with embodiments of the invention.
Figure 2C:
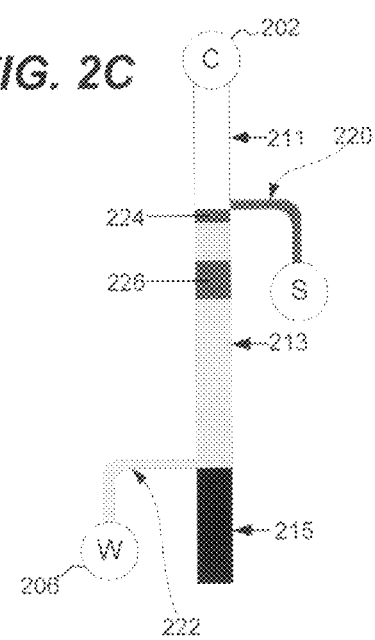

FIG. 2A is a diagrammatic representation of an inline injection DNA-sequencer channel layout according to certain embodiments. The figure shows a main channel 217 having channel regions containing sequencing sample 210, affinity-capture matrix material 212 and denaturing separation matrix 214, respectively. Channels, for example, are etched 30-µm-deep in 100-mm-diameter glass wafers with 1.1 mm drilled cathode 202, sample 204, waste 206 and anode 208 access ports. Sample arm 220 and waste arm 222 leading from the sample port 204 and waste port 206, respectively, are also shown. The sample, capture and separation channel regions are indicated. As is described further with reference to FIGS. 2B-2E, unpurified sample in the sample chamber is driven toward the capture channel region. In one example, the capture channel region contains an affinity-capture matrix that supports an oligonucleotide probe having a selective affinity for the DNA extension fragments in the sample. In general, the capture channel region is the channel or region of a channel containing or configured to contain capture material and containing a sample plug formation zone. The sample plug formation typically takes place in a tight zone within the capture channel region. For example, the sample plug formation takes place in a zone of photopolymerized capture material surrounded by unpolymerized capture material in a capture channel region. One or more capture material inlet and outlet arms may lead from the capture channel region. In the example shown in FIG. 2A, the separation channel is a capillary gel electrophoresis channel.

Figure 2D:
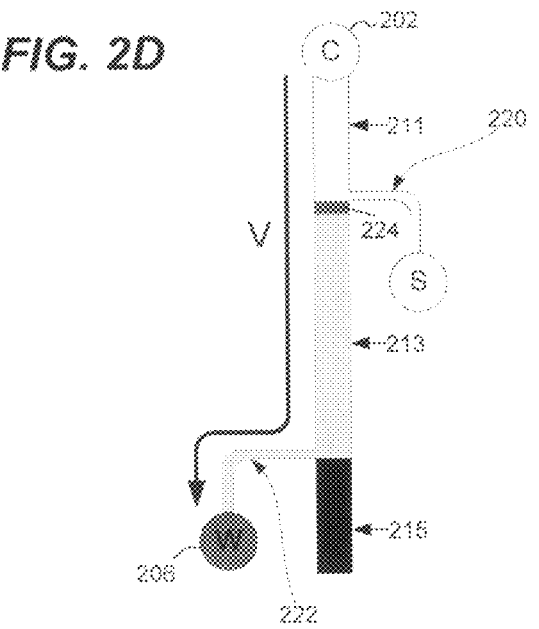
Figure 2E:
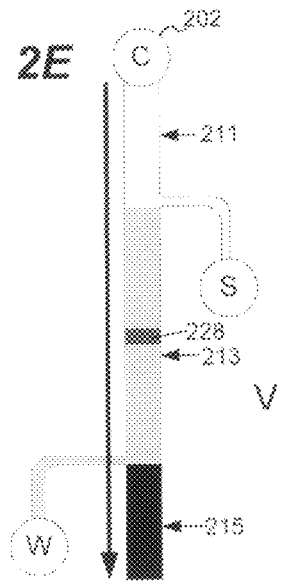

FIGS. 2B-2E are diagrammatic representations of steps in an inline purification, pre-concentration and injection process using the microfluidic channel design shown in FIG. 2A. FIGS. 2B-2E show enlarged representations of the sample, capture and separation regions enclosed by dashed lines in FIG. 2A. The sample channel region 211 is the region downstream of the cathode 202 and upstream of the sample arm 220 inlet; the capture channel region 213 is downstream sample arm 220 inlet and upstream the separation channel 215; and the separation channel 215 is downstream of the waste arm 222 outlet. First in FIG. 2B, by way of example, unpurified sequencing sample (30 mL) is electrophoretically driven toward the affinity-capture matrix at 45° C. by applying a potential between the cathode and the waste port electrode. An arrow indicates the direction of the applied potential V. Then, in FIG. 2C, complementary extension fragments selectively hybridize to the affinity-capture matrix at 224 forming a well-defined inline sample plug. Residual fluorescent reagents, salts and unincorporated nucleotides 226 are not captured by the matrix and migrate toward the waste port 206. FIG. 2D shows excess sample flushed from the sample arm 220 and residual agents electrophoretically washed out of the system through the waste port 206. At 72° C. the purified sample plug releases from the affinity-capture matrix and is injected toward the separation channel 215 using an applied voltage between the cathode 202 and the anode (not shown). This is represented in FIG. 2E, which shows sample plug 228 migrating toward the separation channel region 215 under an applied voltage V.

Because the microfluidic system presented in FIG. 2A eliminates cross-injection geometries and excess sample requirements inherent to cross-injection, the system permits Sanger sequencing miniaturization at a level that is limited primarily by detector sensitivity. A primary design consideration for a microchip sequencing system is the volume of unpurified sequencing sample defined by the sample region dimensions. The minimum necessary volume is dictated by the sensitivity of the detection system and the efficiency of sample processing. For example, considering the case in which the sample channel region is a thermal cycling chamber to produce Sanger extension fragments from template molecules. For a 1,000-base read, a standard cycle-sequencing reaction needs sufficient template to generate 1 billion extension fragments (1 million fluorophores/band×1,000 bands) after 25 cycles. Using a demonstrated linear amplification efficiency of about 70% per cycle, the required number of starting template molecules is about 60 million, or 100 attomoles (60 million template molecules×25 cycles×70% efficiency is approximately 1 billion extension fragments). Typical template concentrations vary from 0.5 nM to 7.5 nM, the optimal amount being a function of template length and purity as well as cycle number and the desire for uniform band intensity. In practice, the reaction volume is held constant while template concentration and cycle number are varied to achieve optimal results. A moderate template concentration of 3.3 nM thus requires 30 mL of sample defined by a 5.3 mm long channel to achieve 100 attomole of template molecules. This analysis, however, assumes near 100% efficiency in transporting the sample from sample channel region (thermal cycling reactor) to the separation channel. Traditional cross-injection from a sample region to a separation channel has an efficiency of about 1%—requiring almost a hundred times the sample region volume. The use of an affinity-capture matrix, e.g., supporting an oligonucleotide that selectively hybridizes to the extension fragments or other analyte, improves efficiency by concentrating and purifying the sample plug, and improves band uniformity and resolution. Using a capture matrix that is not inline to purify and concentrate a sample prior to cross-injection can improve efficiency to about 10%—still below the efficiency required for 100 attomole template molecules.

To achieve the 100 attomole template molecule limit set by the detection sensitivity and thermal cycler reactor constraints, the extension fragments should be captured in a tight zone, desalted, concentrated, and efficiently transported to the separation channel. The system described above with respect to FIG. 2A, in which a capture matrix is inline with the separation channel, with all buffer, regents, etc, washed out eliminates substantially all inefficiency due to transport and impurities. As a result, the required sample region volume is based on the sensitivity of the detection system and thermal cycler efficiency alone. This analysis is not limited to the detection system and thermal cycling efficiency assumptions described above and also can be extended to other detection and sample formation methods and analytes.

Channel Layout and Fabrication

In the inline injection devices and systems described herein, the capture matrix, or a capture channel region containing the matrix and separation channel are configured to inline inject a sample plug into the separation channel. As used herein, inline injection refers to injection of a small, well-defined sample plug contained in the capture channel region into the separation channel region by creating an electric potential across the capture channel and separation channel regions, i.e., a potential between an electrode upstream of the capture channel region and an electrode downstream of the separation channel region.

In certain embodiments, the capture channel region and separation channel region are contiguous, i.e., the capture channel region directly contacts the separation channel region without intervening channels, passageways or any other type of fluidic connections. For example, the capture channel region and separation channel region in FIGS. 2A-2E are contiguous: the capture channel region 213 directly contacts the separation channel region 215. Similarly, in FIG. 7, discussed further below, capture region 722 is contiguous with CE channel 724. In certain embodiments, capture matrix material, e.g., a gel, directly contacts separation matrix material. Contiguous regions may be arranged on a straight, bent or curved line. For example, in certain embodiments, the capture channel region is orthogonal to and contiguous with the separation channel region.

In certain embodiments, the capture channel region and the separation channel region are arranged on a line. This is also depicted in FIGS. 2A-2E. The line may be a straight line, i.e., that is substantially at 180° as shown in FIGS. 2A-2E, or a bent or curved line that deviates from 180° by up to +/−45°. According to various embodiments, a bent or curved line may deviate from 180° by up to +/−30° or up to +/−15° or up to +/−5°. Typically, the capture channel and separation channel regions arranged on a line share a single common axis. Capture channel and separation channel regions arranged on a line may be contiguous, or may be connected by other channels, passageways or any other type of fluidic connections. In certain embodiments, the capture matrix and the separation channel are part of the same etched main channel.

Referring back to FIG. 2A, the capture channel region is contiguous and arranged on a line with the separation channel. See also FIGS. 2B-2E, where the sample plug forms in the affinity capture matrix at 224 in the capture channel region 213, which is contiguous and arranged on a line with the separation channel 215; the matrix and separation channel share a common axis. In FIGS. 2A-2E and in certain embodiments, the matrix and the separation channel are part of the same etched main channel. In many embodiments, the capture channel region 213 directly contacts the separation channel region 215, though in alternate embodiments, the inline capture channel and separation channel regions may be serially arranged channels or chambers connected by other channels or passageways. Typically, however, the capture matrix is placed in the same channel as the separation matrix, with capture matrix material 212 directly contacting the separation matrix 214 or separated only by a short region of buffer or other gel.

In certain embodiments, the sample channel region is also arranged on a line with the capture channel and separation channel regions. In certain embodiments, the sample channel region may also be part of the same main channel, as in FIG. 2A. In other embodiments, the sample channel region may be or include a chamber, e.g., a thermal cycling reactor chamber. See, e.g., FIG. 6 in which a thermal cycler reactor 608 is connected to a capture region 610 via a constriction 614. A waste sidearm is typically located upstream of the separation channel region and downstream of (including even with the end of) the capture channel region. The separation channel region itself may contain tapered turns. Electrodes are positioned upstream of the sample channel region (the cathode), at the sample port, at the waste port and downstream of the separation channel (the anode) in order to electrophoretically drive the unpurified sample, waste material and sample plug between these electrodes as described above with reference to FIGS. 2B-2E.

The microdevice may be fabricated by any appropriate method. To form a microdevice shown schematically in FIG. 2A, for example, channel patterns were photolithographically transferred to a 100-mm-diameter glass wafer (Borofloat, Schott, Duryea, Pa.) and etched to a depth of 30 µm in 49% HF by using a 2,000 Å thick amorphous silicon hard mask. Holes (1.1-mm-diameter) were drilled to create cathode, sample, waste, and anode access ports. Enclosed microfluidic channels were formed through thermal bonding with a blank glass wafer in an atmospheric furnace at 668° C. for 8 hours. Prior to operation, the channel walls were passivated with a modified Hjerten coating to retard DNA adsorption and electroosmotic flow. (Hjerten, *Elimination of Electroendosmosis and Solute Adsorption*. J. Chromatogr. 347: 191-198 (1985), incorporated by reference herein). Sample, capture, and separation channels were 200 µm wide, coupling arms connecting the sample and waste ports to the main channels were 70 µm wide and the tapered turns that fold the CE channel are 65 µm wide. A 5.3 mm sample region (channel region 211 in FIGS. 2B-2E) defines a 30 mL volume. (The determination of sample volume was based on 100 attomoles sample as described above). The channel connecting the sample port to the main channel is shortened in the schematic of FIG. 2A for illustrative purposes; on the microdevice it extended 5.5 cm along the separation channel to provide greater fluidic resistance against hydrodynamic sample movement. The inline affinity-capture matrix region or capture channel region (channel region 213 in FIG. 2B-2E) is 9.9 mm long and the effective separation length of the CE channel is 17.1 cm. As described below, the length of the capture channel region is determined by the amount of capture matrix necessary to bind the 1 billion extension fragments (assuming saturation binding) as well as other design considerations, specifically preventing urea from the urea-containing separation matrix from being present at the formation of the sample plug 228 and reducing matrix movement due to electromigration under the applied potentials. Electromigration may also be retarded by forming a crossliinked gel as the capture gel or by forming nonstraight sides of the channel in the capture region to provide resistance to the motion of the capture gel in the channel.

The separation channel region of the microdevice may be based on previous microfluidic designs for miniaturized Sanger sequencing, where tapered turns that minimize turn-induced band dispersion are utilized to fold a 17.1-cm-long CE channel onto the 100-mm-diameter glass wafer substrate. See Paegel, et al., *Turn geometry for minimizing band broadening in microfabricated capillary electrophoresis channels*. Anal. Chem. 72: 3030-3037 (2000), incorporated by reference herein.

The capture matrix has a selective affinity for the analyte. In many embodiments, the capture matrix includes a gel, bead or other support material that supports a capture compound. For sequencing and other processes in which the analyte are DNA fragments, the affinity-matrix is a gel or material supporting an oligonucleotide that selectively hybridizes to the fragments. The sample is driven into the matrix, which simultaneously performs sample clean-up and defined, ready-to-inject sample plug formation. In many embodiments, the sample plug is thermally releasable from the capture matrix.

In certain embodiments, a capture matrix includes two or more different capture oligonucleotides or other compounds. Such a capture matrix may be used to simultaneously to perform multiplex capture and analysis of different targets.

In addition to gels and beads, any material that supports the oligonucleotide and is able to span the channel may be used in the capture matrix. This includes, but is not limited to, a porous monolith, microfabricated dense posts, polymers beads caught in weirs, magnetically immobilized beads, linear polymers, cross linked polymers, polymers chemically linked to walls, polymers caught in an expanded portion of channel, and polymers grown from the surface of a channel having roughed, e.g., photolithographically roughened, sides.

In certain embodiments, the capture matrix is immobilized. The capture matrix is capable of capturing the thermal cycling products (or other analyte) and desalting them in a zone small enough that provides for good, tight injection. According to various embodiments, the sample plug formation zone (and ready-to-inject sample plug) may range from about 10 microns to millimeters long. In certain embodiments, the sample plug formation zone and (ready-to-inject sample plug) ranges more narrowly from about 50 to 250 microns. See Blazej, R. G., et al., *Inline injection microdevice for attomole-scale sanger DNA sequencing*. Anal. Chem., 79(12): p. 4499-4506 (2007), incorporated by reference herein.

In certain embodiments, the matrix is a highly active polymer network containing a covalently-linked oligonucleotide capture probe. The probe is designed to be complementary only to the cycle sequencing extension products and exhibits minimal self-complementarity. The matrix may be fabricated by incorporating a 5' Acrydite modification (Integrated DNA Technologies) to enable polyacrylamide copolymerization. The affinity-capture matrix may then be synthesized at 4° C. by sparging a 2-mL solution 5% w/v acrylamide, 1×TTE, and 40 nmol of the acrydite-modified oligonucleotide for 2 hours with argon followed by the addition of 0.015% w/v APS and TEMED. The solution is allowed to polymerize for 24 h prior to loading into a 1-mL syringe. Similarly, a linear polyacrylamide sequencing separation matrix may be synthesized at 4° C. by sparging a 10-mL solution containing 3.8% w/v acrylamide, 1×TTE, and 6 M urea for 2 h with argon followed by the addition of 0.015% w/v APS and TEMED. The solution is allowed to polymerize for 24 h prior to loading into a high-pressure matrix-loading chuck. This is described in Scherer, et al. *High-Pressure Matrix Loading Device for Electrophoresis Microchips*. BioTechniques 31: 1150-1156 (2001), incorporated by reference herein.

As indicated above, the volume of the capture channel region is based on the amount of capture matrix necessary to capture the sample analyte. For example, only 83 pL of capture matrix is required to capture 1 billion extension fragments, assuming saturation binding a 20 μM probe nucleotide. In certain embodiments, however, other design considerations may require increasing this volume. First, in embodiments in which the capture channel region is in direct contact with the urea-containing separation matrix, the sample plug formation should be sufficiently distanced from the separation matrix such that diffusion and matrix mixing do not result in denaturing urea present at the point of sample plug formation. Second, if the capture matrix has a charge (e.g., copolymerization with the Acrydite-modified oligonucleotide imparts a negative charge on the capture matrix), electromigration of the bulk matrix under applied potentials may occur. Extending the capture channel region increases fluidic resistance and reduces matrix movement. For the device depicted in FIG. 2A, for example, the capture channel region volume was 56 mL, defined by a 9.9 mm long channel.

In certain embodiments, the capture matrix is physically immobilized to prevent electromigration and provide additional control over sample plug formation location. One method of immobilizing the capture matrix is photopolymerization using a riboflavin photoinitiator. Unpolymerized capture matrix containing acrylamide, an Acrydite-modified capture probe, and the photoinitiator riboflavin is pumped into the capture channel region 213 and waste arm 220 in FIG. 2B. A photomask and UV illumination are used to define a small plug of photo-polymerized capture matrix. This plug functions both as a "gel-valve" to confine the sequencing reaction and also as a definable capture band capable of extension fragment normalization. See Koh, C. G., et al., *Integrating polymerase chain reaction, valving, and electrophoresis in a plastic device for bacterial detection*. Anal. Chem., 2003. 75(17): p. 4591-4598, incorporated by reference herein. See also, Olsen et al., Hydrogel Plugs in Microfluidic Channels., Anal. Chem., 74, 1436-1441 (2002), also incorporated by reference herein. Other methods for immobilizing the capture matrix include physically immobilizing the matrix, e.g., by modifying the sides of the capture channel region to make them fluted or bulbous and/or placing a constriction at the end of the capture channel region. The capture matrix may also be chemically linked to the sides of the capture channel region.

The capability of a matrix formulation to create inline sample plugs suitable for high-resolution separation can be investigated within the microdevice by capturing an unpurified sequencing sample under various binding conditions. Previous work in a cross-injection affinity-capture/CE microdevice demonstrated that extension fragment binding is described by:

$$\frac{\partial}{\partial t}[S(x, t)] = -k_f[S][C] + k_b[S:C] - \mu_S E(x)\frac{\partial}{\partial x}[S(x, t)]$$

where S is the extension fragment, C is the matrix-immobilized complementary oligonucleotide, S:C is the hybridized duplex, $k_f$ and $k_b$ are the respective rate constants for hybridization and denaturation, $\mu_s$ is the mobility constant and E is the electric field in space, x, and time, t. (Paegel, et al., *Microchip bioprocessor for integrated nanovolume sample purification and DNA sequencing*. Anal. Chem. 74: 5092-5098 (2002), incorporated by reference herein). Accessible parameters for optimization are $k_f$ and $k_b$ through probe sequence design and microdevice temperature, [C] in the capture matrix, and the applied E.

Sample plug optimization begins with rational capture matrix design. Provided that the matrix meets specificity and binding capacity requirements, iterative reformulation is not necessary as tuning of hybridization stringency is readily accomplished through external thermal and electric gradients. Theoretical melting temperature calculations can be used to select an extension-fragment-specific, high TM probe oligonucleotide (TM=62° C.) to enhance $k_f$ while still allowing denaturation and sample injection at the CE separation temperature (72° C.). Elevated probe concentration favors forward binding kinetics, increased binding capacity and reduced sample plug size, but also increases gel electromigration effects. A moderate 20 μM concentration in 5% w/v acrylamide may be used to provide stability. Further discussion of matrix design is discussed at Blazej, et al. *Microfabricated bioprocessor for integrated nanoliter-scale Sanger DNA sequencing*. Proc. Natl. Acad. Sci. USA 103: 7240-7245 (2006); Olsen et al. Immobilization of DNA hydrogel plugs in microfluidic channels. Anal. Chem. 74: 1436-1441 (2002); and Paegel et al., *Microchip bioprocessor for integrated nanovolume sample purification and DNA sequencing*. Anal. Chem. 74: 5092-5098 (2002), all of which are incorporated by reference herein.

Inline sample plug formation, injection and sequencing of human mitochondrial hypervariable region II according to an embodiment of the method described with reference to FIGS. 2A-2E were performed. To prepare the DNA template, amplification primers specific to the human mitochondrial hypervariable region II (forward: 5'-AAG CCT AAA TAG CCC ACA CGT TCC-3'SEQ ID NO:1, reverse: 5'-TGG TTA GGC TGG TGT TAG GGT TCT-3'SEQ ID NO:2) were selected using the PrimerQuest program (Integrated DNA Technologies, Coralville, Iowa). The −40 M13 sequence (5'-GTT TTC CCA GTC ACG ACG-3'SEQ ID NO:3) was added to the 5'-end of the forward primer prior to synthesis (Integrated DNA Technologies, Coralville, Iowa) to generate an amplicon compatible with standard sequencing primers. Hypervariable region II DNA is amplified from 20 ng of genomic DNA (#NA-13116; Centre d'etude Polymorphisme Humane, Paris, France) in a 50 µL PCR reaction (0.2 mM dNTPs, 1.5 mM $MgCl_2$, 0.2 µM primers, 20 mM Tris-HCl pH 8.4, 50 mM KCl, and 1.5 U Platinum Taq DNA polymerase; Invitrogen, Carlsbad, Calif.). Following thermal cycling, unincorporated primers, nucleotides, and salts were removed in preparation for cycle-sequencing (QIAquick® PCR Purification Kit #28104; Qiagen, Valencia, Calif.) and PCR yield is quantitated by using the dsDNA intercalating dye PicoGreen (Quant-iT™ PicoGreen® dsDNA Assay Kit #P-7589; Invitrogen, Carlsbad, Calif.) and a FP-750 spectrofluorometer (Jasco, Great Dunmow, Essex, UK) according to manufacture protocols. Template DNA was diluted in 1×TE (10 mM Tris, pH 8.0, 0.1 mM EDTA) to a working concentration of 50 fmol/µL.

Dye primer sequencing reactions were performed by using a cycle sequencing kit (#79260; USB Corp., Cleveland, Ohio) and four energy-transfer (ET)-40 M13 forward primers. (Ju, et al., *Fluorescence Energy-Transfer Dye-Labeled Primers For DNA-Sequencing and Analysis*. Proc. Natl. Acad. Sci. USA 92:4347-4351 (1995)). Each 10-µL reaction consists of 750 fmol of ET primer and 33 fmol of template DNA in a standard sequencing reaction (15 mM Tris-HCL pH 9.5, 3.5 mM $MgCl_2$, 60 µM dNTP, 600 nM ddNTP, 10 U Thermo Sequenase DNA polymerase, 0.015 U *Thermoplasma acidophilum* inorganic pyrophosphatase). Reactions were thermally cycled (95° C. 30 s, 50° C. 30 s, 72° C. 60 s, 35 cycles) by using a Mastercycler™ Gradient and then pooled to make a four-color sequencing sample. Unpurified sequencing sample was stored frozen at −20° C. until use.

To synthesize the affinity-capture matrix, the affinity-capture oligonucleotide (5'-AGA CCT GTG ATC CAT CGT GA-3'SEQ ID NO:4, $T_M$=61.8° C.; 50 mM monovalent salt, 20 µM probe) was selected from the human mitochondrial hypervariable region II DNA sequence 3' of the forward PCR primer. It was designed to be complementary only to the cycle sequencing extension products and exhibit minimal self-complementarity (max=4 base pairs). A polyacrylamide copolymerized matrix supporting the affinity-capture oligonucleotide was synthesized as described above.

The system was first prepared by loading denaturing DNA sequencing matrix from the anode port to the waste arm intersection at 400 psi using the high-pressure loader. Affinity-capture matrix was then loaded with a 1-mL syringe through the cathode port until the capture channel and waste arm are completely filled. Excess affinity-capture matrix in the sample region is removed by flushing 1×TTE from the sample port to the cathode port. All ports were filled with 5×TTE to provide electrophoresis buffering.

The microdevice was transferred to the temperature-controlled stage of the Berkeley four-color rotary scanner (Shi et al. 1999) where the temperature is ramped at 14.5° C./min from room temperature to 72° C.—the CE separation temperature. 1×TTE was again flushed through the sample port to remove affinity-capture matrix that was pushed past the sample arm intersection due to matrix expansion in the CE channel at the separation temperature. The microdevice was then cooled at 2.2° C./min to the 45° C. capture temperature while an 800 V electrophoresis pre-run potential was applied between the cathode and anode. Unpurified sequencing sample was loaded into the 30-nL sample region by pipetting 1 µL of the unpurified sequencing sample into the cathode port and applying 58 kPa vacuum to the sample port for 2 seconds. The cathode port was then washed 3× with 10 µL of 5×TTE to remove remaining sequencing sample. Equal 10 µL volumes of 5×TTE were placed on the cathode and sample ports to prevent hydrodynamic flow.

Figure 3:
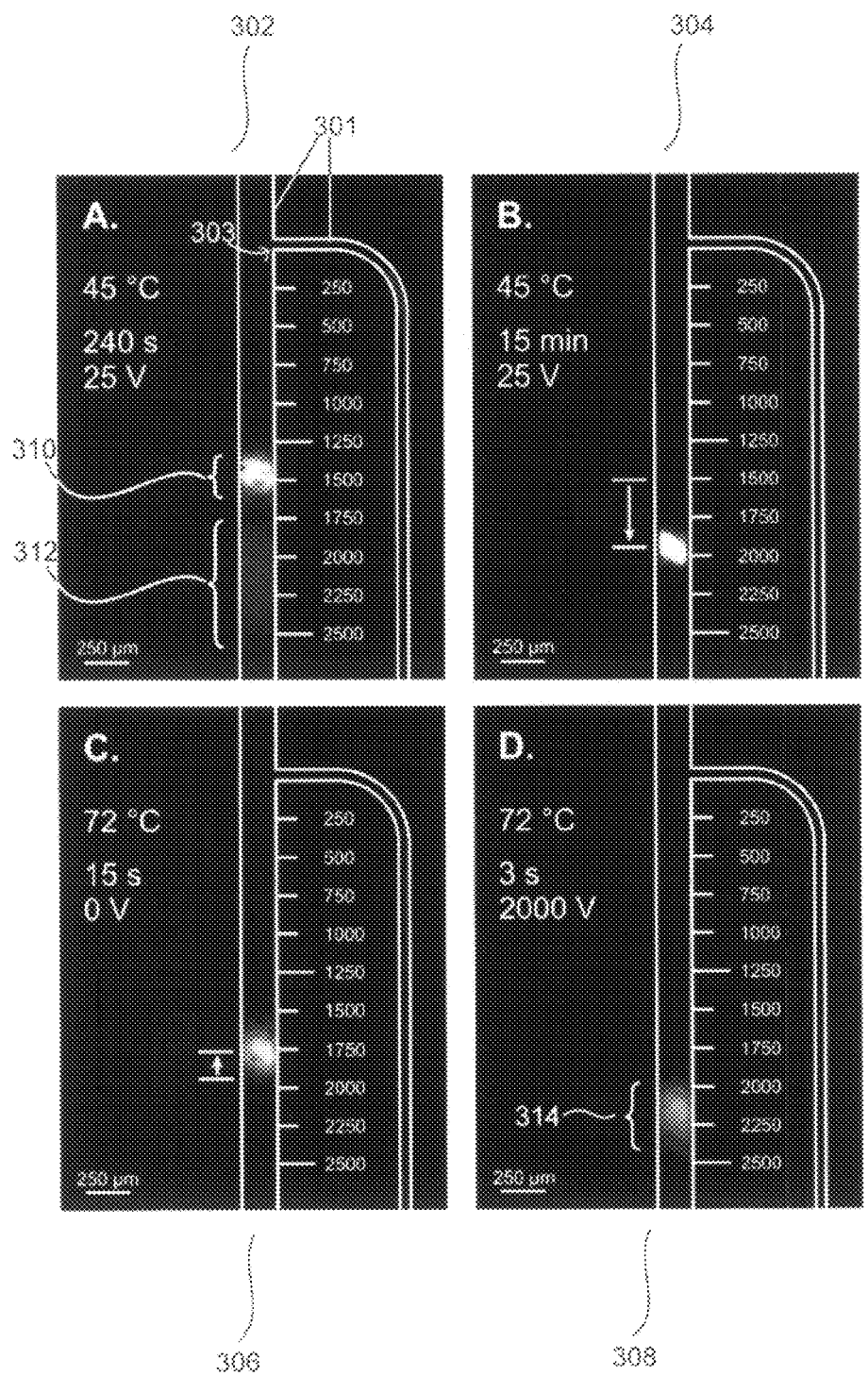
FIG. 3 are fluorescent images of a device in accordance with embodiments of the invention during inline sample plug formation and injection.

FIG. 3 presents fluorescent images fluorescent images of the device during inline sample plug formation and injection. Microfluidic channels 301 are outlined in white, the scale indicates displacement in µm from the sample arm junction 303 and arrows indicate direction of sample plug migration. Inline sample plug formation was initiated by grounding the cathode and applying 25 V to the waste. Image 302 shows the sample plug 310 and residual reagents 312 200 seconds after plug formation was initiated at 45° C. by applying 25 V between the cathode and waste ports. After extension product capture was complete in 240 s, 1×TTE was flushed through the sample port to remove any sequencing sample remaining in the sample arm. The 25 V potential was then reapplied for 15 min to electrophoretically wash interfering residual reagents out of the capture channel. Image 304 shows that the negatively charged sample plug and capture matrix have migrated 400 µm toward the waste port after 15 min of electrophoretic washing. Alternatively, the capture matrix may be physically immobilized, e.g., by photoinitiated polymerization, as discussed above. The stage was ramped to 72° C. to release the sample plug from the affinity-capture matrix. Image 306 shows the sample plug released from the capture matrix and shifted toward the cathode due to separation channel gel expansion. CE separation was accomplished by grounding the cathode and applying 2000 V to the anode. Image 308 shows that application of the separation electric field (100 V/cm) between the cathode and anode causes the sample plug 314 to elongate as it begins to size-fractionate. Four-color sequence data were collected in 32 min by the Berkeley four-color rotary scanner and processed with the Cimarron 3.12 base caller (NNIM, Sandy, Utah).

Figure 4:
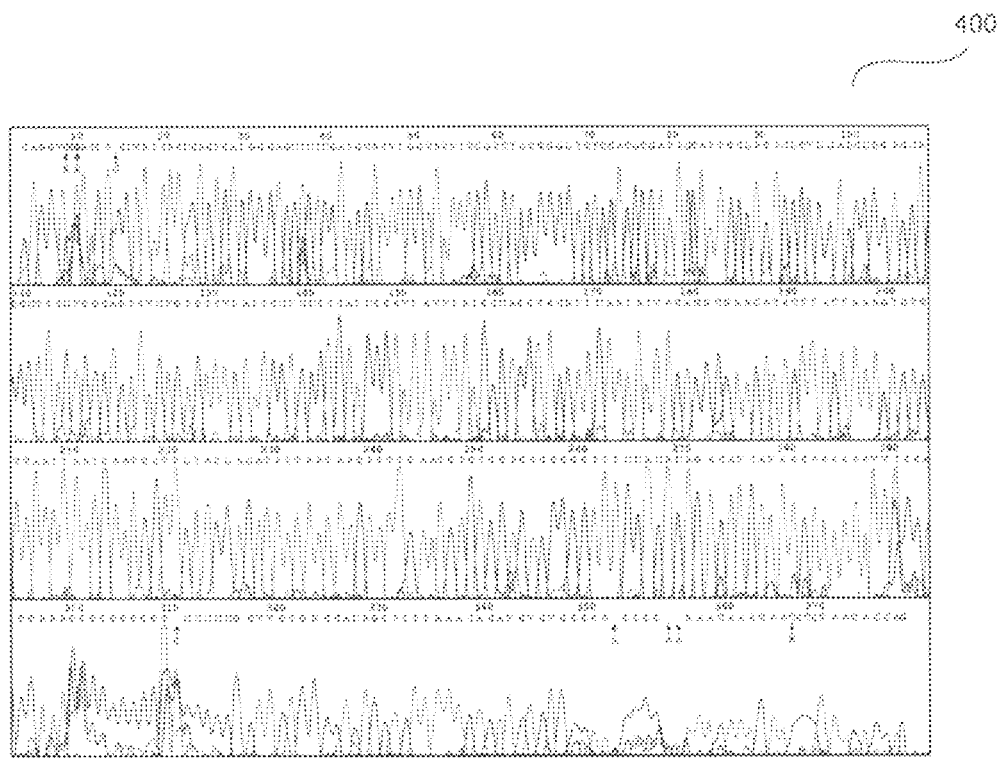
FIG. 4 presents data from sequencing of human mitochondrial hypervariable region II from about 100 attomoles (60 million molecules) of DNA template using an inline injection system and method in accordance with the invention.

FIG. 4 presents the inline-injected sequence data 400 from 30-nL of sequencing sample of 100 attomoles (60 million molecules) of DNA template. Arrows indicated base call errors with correct calls given below and "x" indicates an inserted base. Using a 99% accuracy cutoff with the known mitochondrial sequence, automatic base-calls produce a read length of 365 bases. The probe oligonucleotide is internal to the 455 bp amplicon and hybridizes extension fragments 52 bases or longer from the 18-base sequencing primer initiation site for a total possible read length of 386 bases. Three consecutive runs performed under substantially identical conditions exhibited excellent uniformity generating 371 ($\sigma$=2.6)

correct base calls. Importantly, unlike cross-injected CE separations, no optimization of injection timing was necessary to achieve this base-call consistency because separation is initiated by direct application of the CE field to the inline sample plug.

Microbead-based Inline Injection System

Another aspect of the invention relates to an integrated, microbead based inline injection sequencing device, method and system. The microfluidic system utilizes emulsion amplified clonal microbeads to provide a DNA template for efficient genome sequencing. A microfabricated integrated DNA analysis system (MINDS) using microbead elements as cloning templates is described in commonly assigned U.S. patent application Ser. No. 11/139,018 (U.S. Patent Publication No. US-2005-0287572-A1), incorporated by reference herein. As described therein, the MINDS method, process, and apparatus include a microfabricated structure on which thermal cycling, affinity capture, sample purification, and capillary array electrophoresis (CAE) components are integrated. Microreactor elements carrying multiple copies of a clonal sequencing template are distributed via a distribution channel into a plurality of thermal cycling chambers. Only one microreactor element is passed into one thermal cycling chamber. Thermal cycling extension fragments are produced from that microreactor element in each chamber. Purification chambers are connected to the thermal cycling chambers to capture and concentrate the extension fragments. Component separation channels are connected to the purification chambers to analyze the extension fragments. In the embodiments presented herein, the purification chamber (capture channel region) is inline with the separation channel for inline purification and injection.

Figure 5:
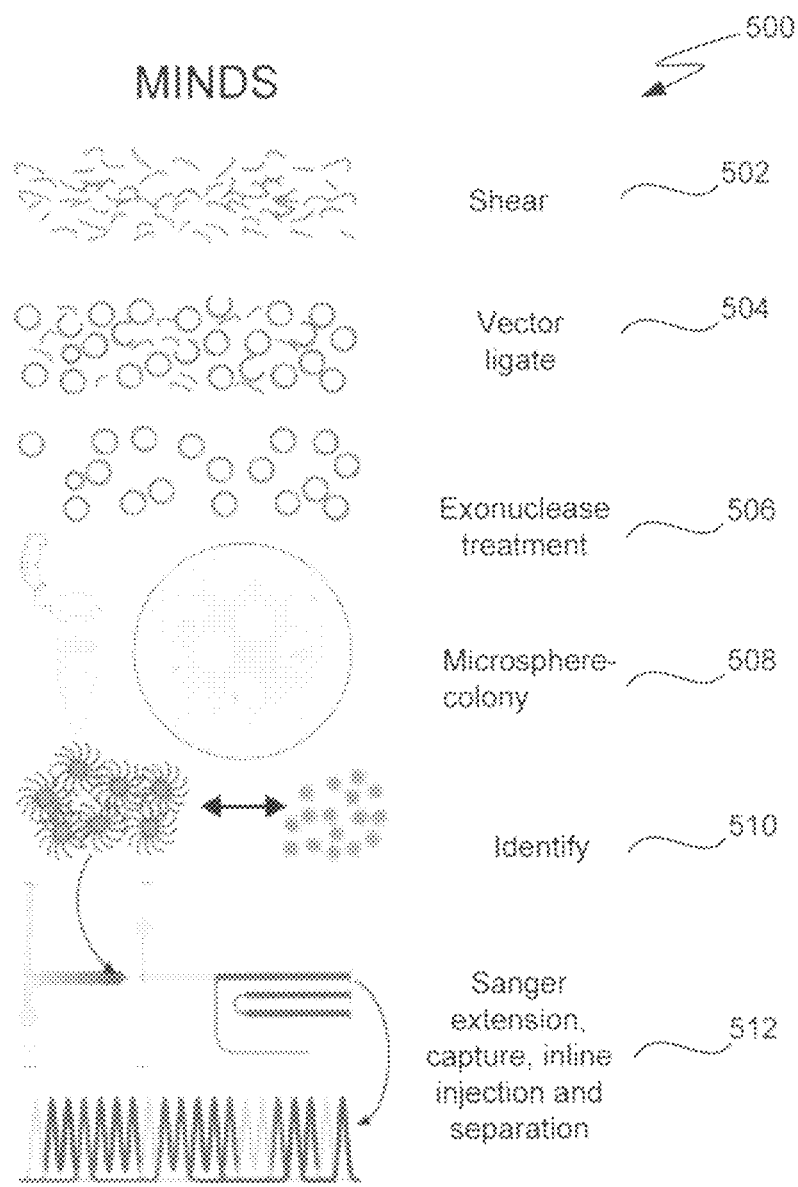
FIG. 5 is a diagrammatic representation of steps involved in a genome sequencing process in accordance with the present invention.

FIG. 5 shows an overview of one embodiment of a MINDS process. As shown by FIG. 5, the MINDS process, in one embodiment, begins with the shearing of DNA into DNA fragments at step 502. The fragments are then ligated to form a mixture of desired circular and contaminating linear products at step 504. The contaminating linear products are then selectively removed, for instance, by exonuclease degradation at step 506. A colony of microspheres or microbeads carrying multiple clonal copies of a DNA sequencing template is next formed at step 508. The colony may be generated, for example, by emulsion PCR reactions. The microbeads having a DNA sequencing template are then identified at step 510. The microbeads may be identified by a fluorescence activated cell sorting (FACS) technique. Only one such run is required, and it may take 6 hours or less to complete. The microbeads with the DNA sequencing templates are then distributed into a microfluidic structure for integrated sequencing reaction (thermal cycling), purification, inline injection, and capillary electrophoresis at step 512. The process eliminates the laborious, expensive, and time consuming in vivo cloning, selection, colony isolation, and amplification steps of conventional sequencing. Instead, these steps are replaced with readily miniaturized and automated in vitro steps.

A microcarrier element within a microreactor element may be used to carry the multiple copies of the clonal sequencing template. The microreactor element is a bolus or microemulsion droplet. The microreactor element includes a microsphere or a microbead carrying the multiple copies of the clonal sequencing template. The sequencing template is a DNA or RNA sequencing template.

Microbeads are ideal carriers, providing flexible control over size, surface, fluorescent, and magnetic properties. Miniaturization of a sequencing reaction chamber through microfabrication and the concomitant reduction in reagent volume makes possible the use of a single, clonal microsphere as a carrier for sufficient DNA sequencing template. This enables the use of a matched process flow that permits selection, amplification and sorting of clonal templates for direct integration with a nanoliter extension, clean-up and sequencing process. Because microbeads can only bind a limited amount of DNA template, efficient, integrated systems are required for microbead-based Sanger sequencing.

The devices, methods and systems of embodiments of the invention utilize inline injection of the thermal cycling reaction products into the separation channels. As discussed above, inline injection allows performing Sanger sequencing, sample purification/concentration and electrophoretic analysis from only 100 attomoles of starting template—efficiency that is not approached with previous microdevice systems.

Figure 6:
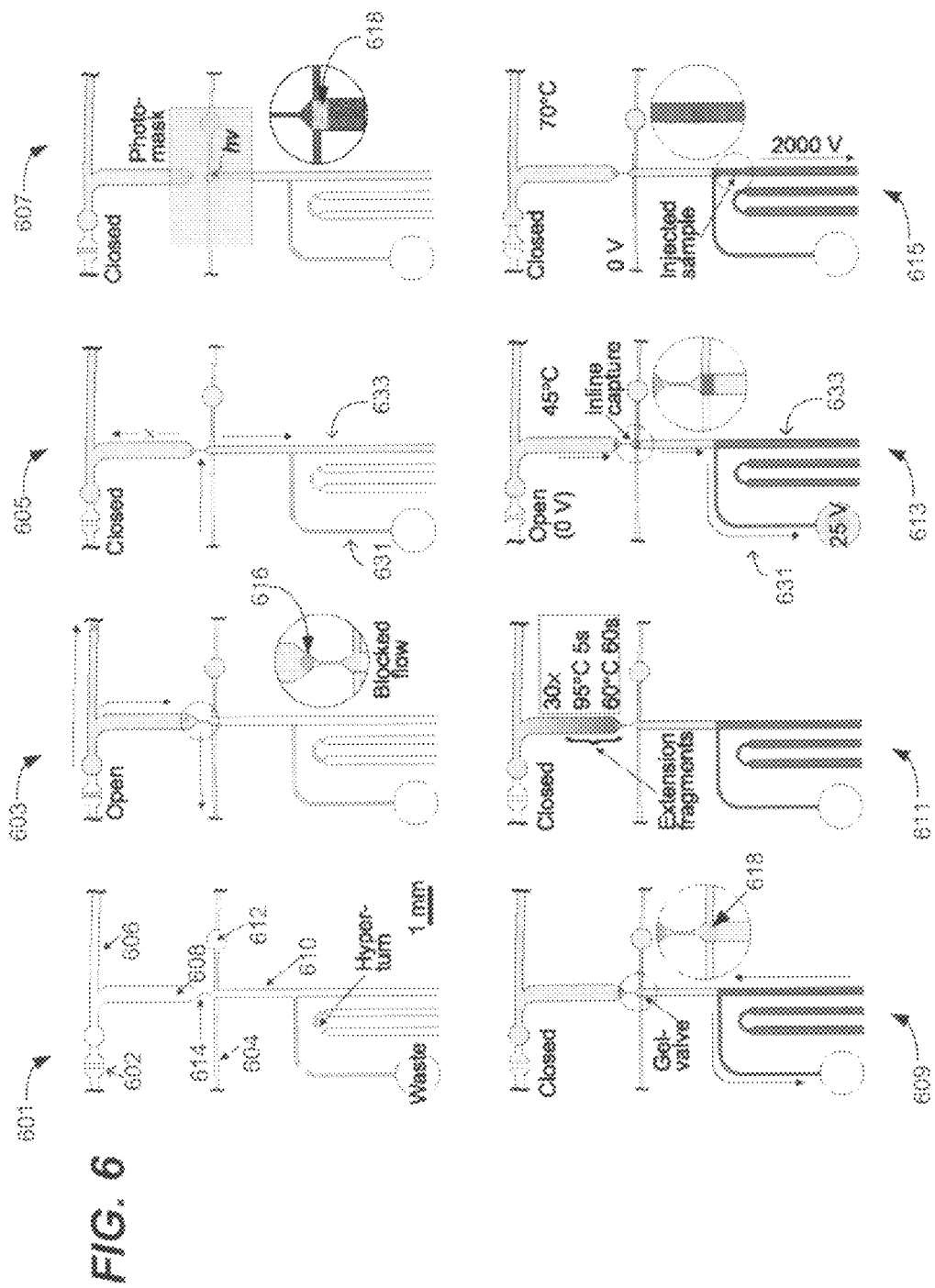
FIG. 6 is a diagrammatic representation of microfluidic circuitry and process flow for a microbead-based sequencing process in accordance with embodiments of the invention.

FIG. 6 is a diagrammatic representation of steps involved in a genome sequencing process of a single functional element of a parallel processing array in accordance with the present invention. At 601, the single functional element is shown prior to the introduction of the sequencing reagent containing microbeads, the capture matrix, and the gel separation matrix. The device includes multiple glass layers, including a bottom and top layer. A bottom-layer microvalve 602 and a capture matrix bus 604 are connected to a top layer reagent bus 606, a reaction chamber 608, and a capture channel region 610 by a via hole 612. The capture channel region is next to the CE channel. In many embodiments, the microvalve 602 is not associated only with a single functional element, but used to introduce sequencing reagent into the reagent bus for all elements in the array. In alternate embodiments, each functional element has a valve that controls the connection of the associated reaction chamber with the distribution channel. In certain embodiments, there is a valve at end of chamber in place of constriction 614. These two valves at the top and bottom of reaction chamber can be controlled together or separately.

The integrated sequencing process begins by loading clonal template microbeads into individual reactors. A number of technologies exist to accomplish this task, including on-chip cell sorting by imaging or optically detecting the fluorescence or light scattering or refraction of the bead combined with individual or multiplexed microvalves to actively confine microbeads in individually addressable reactors by closing off the reactor inlet, outlet or both. A simpler and perhaps as effective approach is to use the microbead to self-regulate, or "auto-valve", the filling process. This is illustrated at step 603. Microbeads are loaded into the system by opening a single microvalve 602 at the system input and introducing sequencing reagent containing microbeads into the reagent bus 606 while applying vacuum to the capture matrix bus 604. Arrows indicate the direction of fluid flow. Reagent is drawn into the reactor 608 until a microbead blocks the constriction engineered into the end of the reactor, thus preventing additional microbeads from entering. See the inset in which microbead 616 blocks the constriction at the end of the reactor. If a sufficiently dilute microbead solution is used, a single microbead can be loaded into each reactor, as modeled by the Poisson distribution, without the need for active external control. In alternate embodiments, the beads are distributed via active control. In certain embodiments, active control involves sensing when a microbead has entered the distribution channel, closing the distribution channel exit valve at that time, identifying an empty (non-microbead containing) thermal cycler reactor to distribute the bead to, and opening inlet and outlet valves associated with the identified thermal cycler reactor to allow distribution of the bead into that reactor. The inlet and outlet valves are then closed to trap the bead within the thermal cycler reactor for thermal cycling.

Once all of the microbeads are loaded, the microvalve is closed to prevent backflow. According to various embodiments, a valve may be located at each end of reactor, or only at either end of the reactor. An unpolymerized capture matrix containing an acrylamide, Acrydite-modified capture probe, and the photoinitiator riboflavin is pumped into the capture matrix bus, filling the CE channel 633 and the waste arm 631. This is shown in step 605. Arrows indicate the direction of fluid flow, with the absence of backflow indicated by the arrow with an "x." Upstream of the constriction, the reaction chamber and reagent bus are filled with reagent; downstream of the constriction, the CE channel and waste arm are filled with the capture matrix material.

A photomask and UV illumination are used to define a small plug of photo-polymerized capture matrix 618 at the top of the CE channel as described above and in step 607. This plug functions both as a "gel-valve" to confine the sequencing reaction and also as a definable capture band capable of extension fragment normalization. The inset shows the portion 618 exposed to UV light to form the plug.

The microdevice is primed for Sanger sequencing by loading a low-viscosity separation matrix from the common anode (not shown), displacing unpolymerized capture matrix in the CE channel into the waste port. This is shown in step 609, with the arrows indicating the direction of flow of the separation matrix into the CE channel 633 and the waste arm 631.

Extension fragments are generated from each clonal microbead by thermal cycling the reactor (35×95° C. 5 s, 60° C. 60 s) in step 611. In the embodiment depicted, a single microvalve is used to seal the reagent bus in combination with photopatterned gel-valves and simple diffusional trapping. As indicated above, valves at each end of the thermal cycler reactor may be used for trapping as well.

Once thermal cycling is complete, the reagent bus microvalve is opened and the bus is electrically grounded in step 613. Inline capture is performed at 45° C. as described above with reference to FIG. 2B by applying 25 V to the waste port to drive the extension fragments into the capture matrix. Since only a small plug of the capture matrix is immobilized by photo-polymerization, the residual Acrydite-modified capture probe that is not copolymerized in this plug will electrophoresis towards the waste along with residual Sanger sequencing reagents and excess extension fragments. The photo-polymerized plug, therefore, defines the absolute size of the sample injection plug and acts to normalize extension fragment concentration across all reactors.

The final step is to release and inject the purified and normalized inline sample plugs by raising the microdevice temperature to 70° C. and applying a 2,000 V separation voltage to the common anode (not shown) in step 615. The matrix bus is utilized as the cathode by electrically grounding the matrix port. While the reagent bus could potentially serve the same purpose, the auto-valve constriction may cause current instability at the high-fields used in capillary electrophoresis.

Figure 7B:
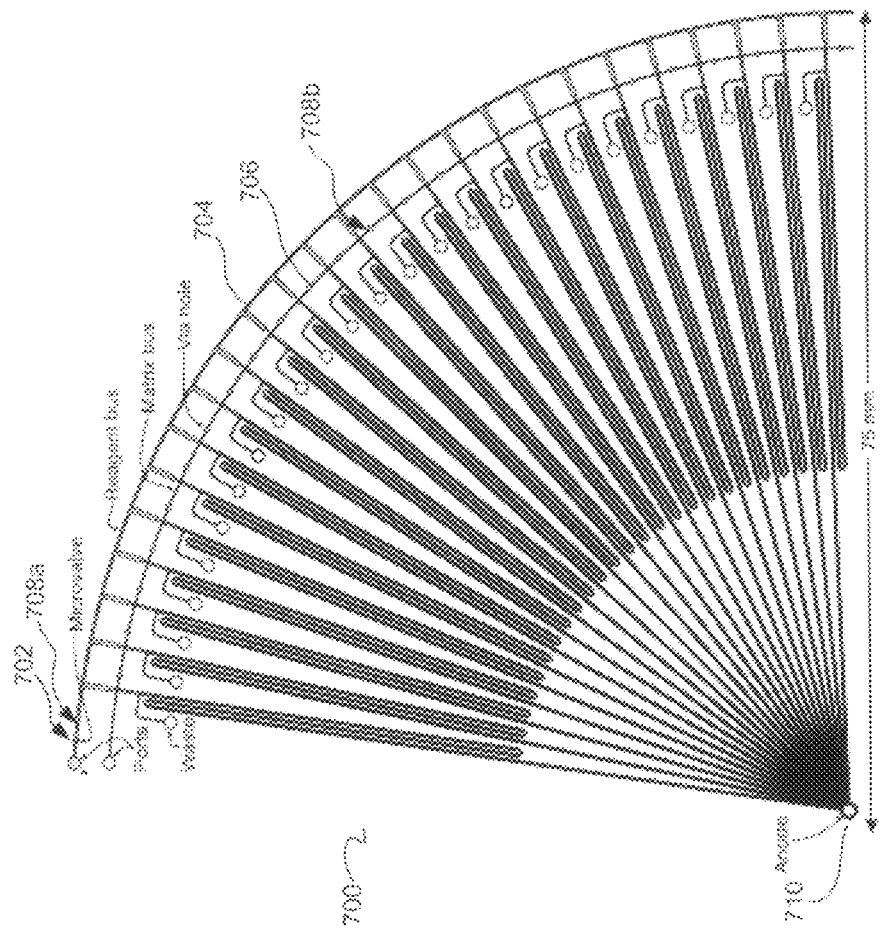
FIG. 7B is a diagrammatic representation of one quadrant (25-elements) of a 100-element radial array designed to fit on a 150 mm diameter wafer.
Figure 7A:
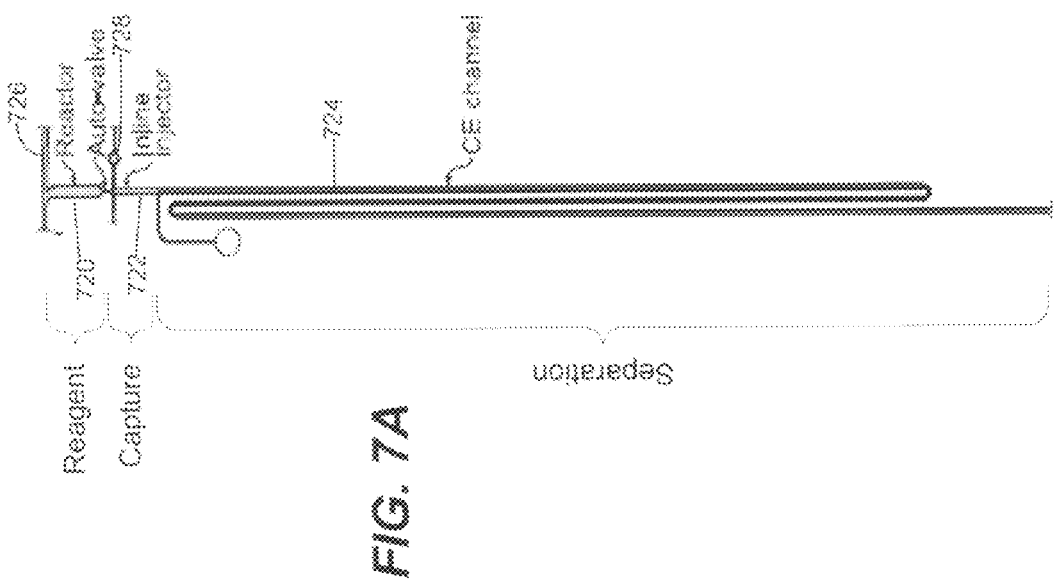
FIG. 7A is a diagrammatic representation of a functional element of a parallel processing array containing the microfluidic structures for microbead isolation, thermal cycling, inline injection and high performance capillary electrophoresis in accordance with embodiments of the invention.

FIG. 7A is a diagrammatic representation of a functional element of parallel processing array, such as that discussed with respect to FIG. 6, containing the microfluidic structures for microbead isolation, thermal cycling, inline injection and high performance capillary electrophoresis. Reagent (sample) 720, inline capture 722 and separation channel 724 regions are indicated. This is similar to the channel layout presented in FIG. 2A, with sequencing reagent bus or distribution channel 726 and capture reagent bus or distribution channel 728 added to connect the element to the parallel processing array. The sample channel region in FIG. 7A is a thermal cycling reactor. FIG. 7B is a diagrammatic representation of one quadrant (25-elements) 700 of a 100-element radial array designed to fit on a 150 mm diameter wafer. Each element contains a reactor (sample channel region), inline injector (capture channel region), and capillary electrophoresis channel (as shown in FIG. 7A), and the individual elements are linked by a reagent bus or distribution channel 704, matrix bus or distribution channel 706 and common anode 710. A single microvalve 702 is used to seal the reagent bus. Via hole 708a connects the microvalve 702 to the reagent bus 704. Via hole 708b connects the capture matrix bus 706 to the main channel containing the inline injector and CE channel. For direct sensing and distribution, a valve for each reactor on distribution channel may be used.

The inline injectors described herein allow high densities of elements to be place on a wafer or other substrate. According to various embodiments, parallel processing arrays on a wafer or other substrate, such as those discussed with reference to FIGS. 7A and 7B, may have densities of at least 0.1 per cm$^2$ of substrate; at least 0.5 per cm$^2$ of substrate; at least 1 per cm$^2$ of substrate; at least 2 per cm$^2$ of substrate and at least 5 per cm$^2$ of substrate.

Linked sequencing of both template ends, or "paired-end sequencing", provides valuable genome assembly information. Because the insert size is known from the library creation step, paired reads provide the assembler with relative distance and orientation information. Additionally, in genomes containing high repeat content, such as the human and other mammalian genomes, a read falling in a repeat region can be anchored within the genome assembly if the paired read contains unique sequence data.

Figure 8:
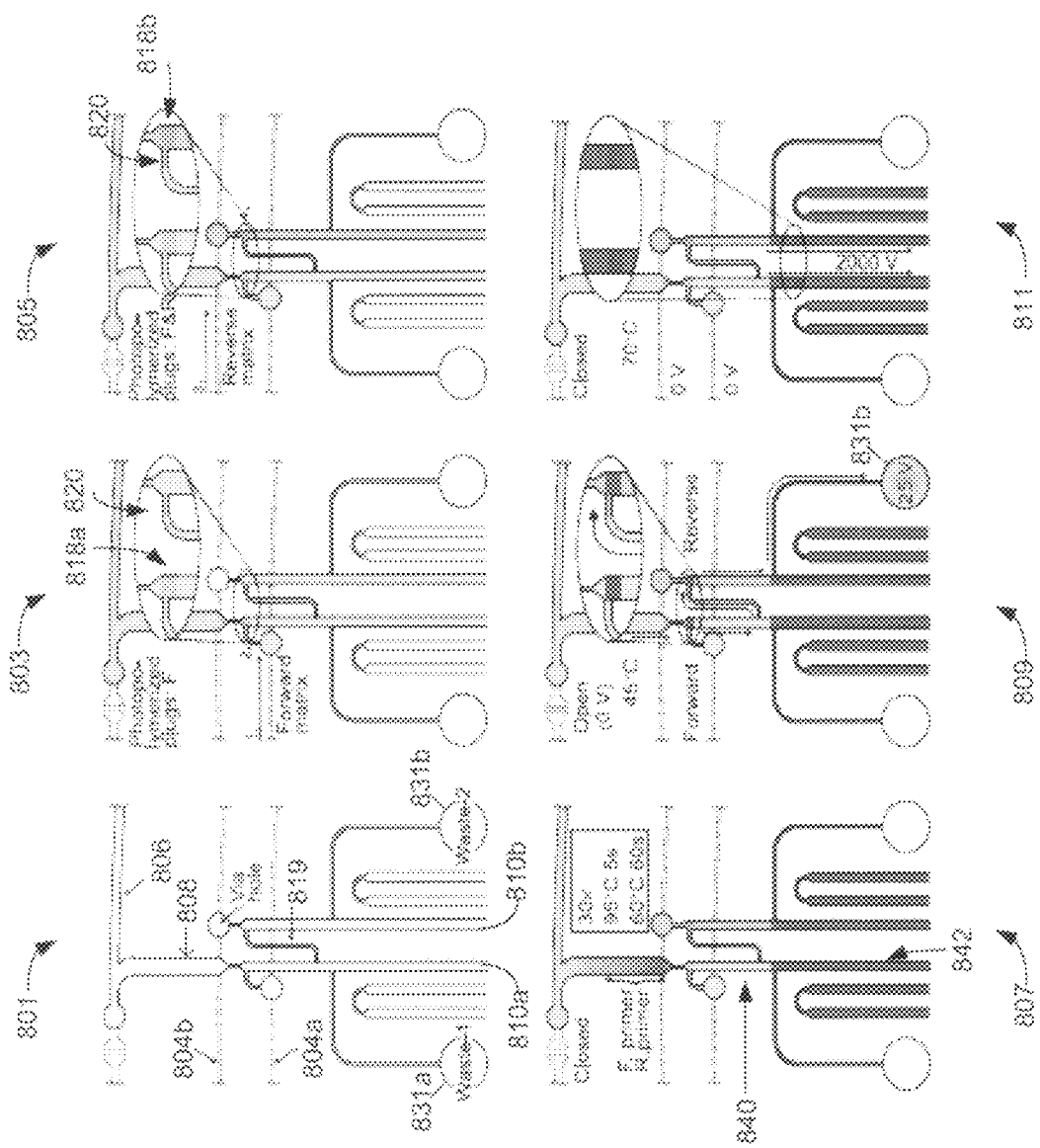
FIG. 8 is a diagrammatic representation of microfluidic circuitry and process flow for a paired-end sequencing process in accordance with embodiments of the invention.

The exquisite sequence specificity of DNA hybridization utilized in the inline affinity-capture injection system can also be used to segregate a simultaneous forward and reverse paired-end sequencing reaction. FIG. 8 presents microfluidic circuitry and process flow for integrated paired-end sequencing. The design is similar to that presented in FIG. 6 with the addition of a second matrix bus 804b, waste port 831b, and CE channel 810b. The channel design is shown at 801 prior to the introduction of sequencing reagent, capture matrix, or gel separation matrix. The functional element has a single thermal cycling element 808 connected to two inline injection CE systems, including CE channels 810a and 810b utilizing forward and reverse capture matrices. Reagent bus 806 distributes a microbead to a thermal cycling reactor 808, as in FIG. 6. Forward (F) matrix bus 804a is configured to pump forward (F) capture matrix material into the forward (F) capture channel region of a CE channel 810a; reverse (R) matrix bus 804b is configured to pump reverse (R) capture matrix material into the reverse (R) capture channel region of a CE channel 810b. A transfer arm 819 connects the forward and reverse capture channel regions. The microdevice is primed with microbeads as before except that the sequencing reagent now contains both forward and reverse sequencing primers.

In step 803, forward capture matrix, containing an Acrydite-modified probe complementary only to the forward extension fragments, is pumped into the Forward (F) matrix bus 804a and gel-valve capture plugs are photopatterned both at the top of the capture channel region of the CE channel 810a as well as in the transfer arm 819. The gel-valve capture plug in the CE channel 810a is indicated at 818a. The gel-valve plug 820 in the transfer arm is formed at the outlet to the reverse capture channel region. Similarly, reverse capture matrix, containing an Acrydite-modified probe complementary only to the reverse extension fragments, is pumped into the Reverse (R) matrix bus 804b and photopatterned at the top of the CE channel 810b in step 805 to form gel-valve capture plug 818b. The gel-valve 820 in the transfer arm prevents reverse capture matrix from entering the forward CE channel 810a. A separation matrix is loaded from the common anode (not shown) and a simultaneous forward and reverse sequencing reaction is performed in step 807. A forward capture channel region 840 and separation channel region 842 are indicated. Segregation and capture of the forward and reverse extension fragments is accomplished by electrically grounding the reagent bus and applying 25 V to the waste port 831b of the reverse channel 810b in a step 809. Extension fragments are serially drawn first through the forward capture matrix then through the transfer arm and finally through the reverse capture matrix. Segregated forward and reverse extension fragments are released from their respective capture matrices at 70° C. and inline-injected into distinct CE channels for paired-read sequencing in step 811. Other sequencing designs and process flows may be used in the inline injection methods and devices described herein. For example, Blazej, et al. *Microfabricated bioprocessor for integrated nanoliter-scale Sanger DNA sequencing*. Proc. Natl. Acad. Sci. USA 103: 7240-7245 (2006), incorporated by reference above, describes bioprocessor components that for use with a cross-injection system. These components may be used in accordance with the inline injection systems described herein.

Microbead Droplet Generator

Returning back to FIG. 5, the MINDS process involves generating microbead carrying multiple clonal copies of a DNA sequencing template in step 508. Microemulsion droplets are a powerful approach for efficiently performing PCR amplification of small amounts of template in a massively parallel format. This approach is valuable because: (1) the template and its PCR progeny are contained in a small nanoliter (nL) volume emulsion particle, enabling efficient amplification to produce a PCR colony contained in the bolus and chemically linked to a bead; (2) the isolated emulsion particles reduce contamination and false amplification by separating the various amplification reactions; (3) the comparatively high concentration of a single template target in these nL bolus enables single molecule/single target amplification; and (4) the use of emulsion particles enables the massively parallel PCR amplification and analysis of large numbers of targets. Conventional methods for producing PCR emulsions are very empirical, typically produce very small emulsion droplets, and produce a wide range of droplet sizes. U.S. Provisional Application No. 60/962,059, filed Jul. 26, 2007, incorporated herein by reference, describes a microfabricated nozzle or droplet generator (µDG) that can produce user controlled, uniform size emulsion particles for performing PCR. The high-throughput engineered nanoliter emulsion generator allows for the introduction of a single functionalized microbead and a single DNA template or cell in individual, controlled size droplets.

FIGS. 9A and 9B present a schematic of a method of producing nanoliter emulsion particles. Stochastic limit dilutions of both beads and target molecules allow encapsulation of a primer-functionalized bead and the target in individual droplets. PCR reagent, target molecules and reverse primer attached beads (at 902) mixed at a statistically dilute level produce 1% of the droplets at 904 with both a cell and a bead functionalized reverse primer. A droplet with both a cell and bead is shown at 906. FIG. 9B illustrates the reverse primer attached bead and target (cell/DNA fragment) in a droplet, with dye labeled forward primers at 908. Amplification in the droplet produces a large number of double stranded products that are linked to the bead by the covalent reverse primer at 910. Dye labeled forward primers in solution allow for fluorescence detection of beads populated with the amplified target molecule. A bead with a large number of fluorescently labeled double stranded products is shown at 912.

Figures 10A, 10B:
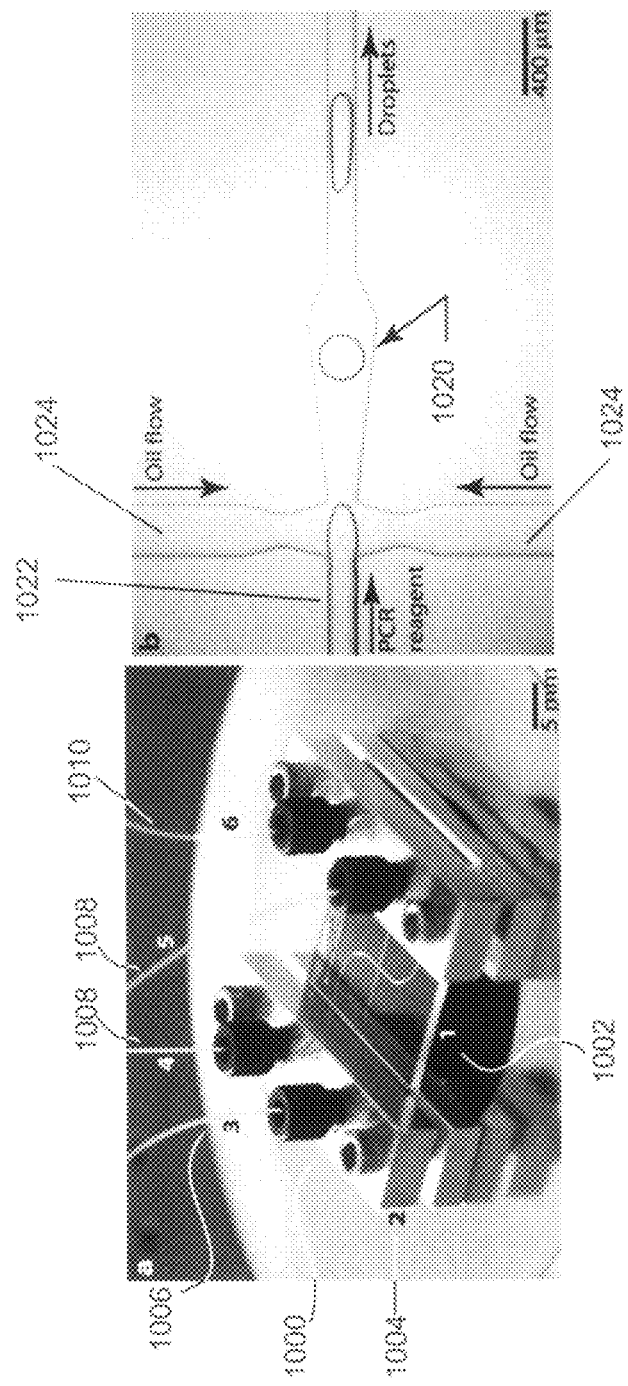
FIG. 10A is a photograph of a microfabricated emulsion generator device that may be used in accordance with embodiments of the invention.
FIG. 10B is an optical micrograph of droplet generation at the nozzle.

FIG. 10A shows a photograph of a microfabricated nozzle device 1000 that rapidly generates controlled, nanoliter volume droplets of PCR reagent in emulsion oil and routes them into a 0.6 mL tube for temperature cycling using a block thermal cycler. The microdevice includes oil and aqueous fluidic interconnections, along with the droplet outlet tubing. Microfabricated chip 1002, fluid interconnect 1004, PCR mix inlet microtube 1006, emulsion oil inlet microtubes 1008 and PCR droplet outlet 1010 are indicated. Accurate infusion of oil and aqueous phases is enabled by the use of syringe pumps (PHD 2000, Harvard Apparatus) and glass syringes (Gastight syringe, Hamilton Company). Microtubing (Peek tubing, Upchurch Scientific) with about 100 µm internal diameter is used to minimize dead volume in the connections. FIG. 10B shows an optical micrograph of droplet generation at the cross-injector nozzle 1020. PCR reagent is injected in the left channel 1022, while emulsion oil is injected in the top and bottom channels 1024. Droplet breakage at the nozzle occurs as a result of competition between viscous stresses associated with the imposed flow field and capillary stresses due to surface tension between the two phases. Further, surface modification with octadecyltrichlorosilane renders the channel walls, which may be glass, hydrophobic, thereby aiding in droplet formation and preventing any droplet-wall interaction downstream. This is important for preventing cross-contamination between droplets. The oil-surfactant combination used for emulsion generation is also important from two standpoints. First, it should allow droplet formation and maintain droplet stability through temperature cycling. Second, it should be compatible with single molecule analysis by minimizing enzyme/DNA adsorption to the active oil-aqueous interface. Various oil-surfactant combinations have been explored in literature for microfabricated emulsion generation and show stable droplet formation but exhibit a high degree of enzyme adsorption. Two oil-surfactant formulations: (1) Mineral oil, 4.5% (v/v) Span 80, 0.4% (v/v) Tween80 and 0.05% (v/v) Triton X-100 (all Sigma) (Ghadessy, et al., Directed evolution of polymerase function by compartmentalized self-replication. Proc. Natl. Acad. Sci. U.S.A. 2001, 98, 4552-4557; Dressman et al., *Transforming single DNA molecules into fluorescent magnetic particles for detection and enumeration of genetic variations*. Proc. Natl. Acad. Sci. U.S.A. 2003, 100, (15), 8817-8822, incorporated by reference herein) and (2) 40% (w/w) DC 5225C Formulation Aid (Dow Chemical Co., Midland, Mich.), 30% (w/w) DC 749 Fluid (Dow Chemical Co.), and 30% (w/w) Ar20 Silicone Oil (Sigma) (Margulies et al. *Genome sequencing in microfabricated high-density picoliter reactors*. Nature 437, 376-380 (2005)) have been successfully used for single molecule DNA amplification/analysis in a conventional polydispersed emulsion PCR format.

The emulsion oil formulation presented by Margulies et al., referenced above, was used to show stable droplet formation as well as successful amplification from a single DNA molecule in uniform volume nanoliter droplets. Reaction volumes of 1-5 mL were used, as they contain more than 10 fold excess reagent for efficient amplification of >1000 bp amplicons and at the same time are small enough to keep the effective concentration of the single DNA molecule high (0.5-1.5 fM). Control over droplet size and generation frequency is achieved by (1) controlling the channel dimensions at the nozzle and (2) by varying the relative flow rates of oil and PCR reagent. Standard glass microfabrication may be used to etch the nozzle shown in FIG. 10B to a depth of 65 μm. Access holes (500 μm diameter) are drilled and enclosed channels are formed by thermally bonding the patterned glass chip with another glass slide. Using this device, three different droplet sizes—1.1 mL, 2.2 mL and 4.0 mL—were generated by varying the total oil flow rate between 4.0, 2.0 and 1.0 μL/min, respectively, while keeping the PCR reagent flow rate constant at 0.5 μL/min. All the droplet sizes show remarkable stability after 40 cycles of PCR.

To validate the usefulness of the μDG for single molecule genetic analysis, a 1,008 bp region of the pUC18 genome was amplified from three different stochastic-limit template dilutions in 2.2 mL droplets. Following PCR, droplets were purified to remove the oil phase and the extracted amplicons were run on an agarose gel. Gel quantitation showed three to five attomoles of product per template molecule consistently generated for the three different starting average template concentrations of 0.67, 0.067 and 0.0067 molecules/droplet. In particular, clear production in the lanes showing PCR amplified product produced from 1600 and 3200 droplets with corresponding concentrations of 0.067 and 0.0067 strands per droplet, respectively, demonstrates that full length 1 kb amplicons appropriate for sequencing can be produced from single template molecules in individual emulsion bolus. However, the PCR yields were about 20 fold lower than required by the attomole-scale inline-injection sequencing device. Two reasons for this low yield are (1) DNA template and enzyme adsorption to the glass syringe wall and (2) enzyme adsorption to the oil-aqueous interface in the high surface area to volume ratio droplets. The syringe can be coated with PEG-silane, poly-N-hydroxyethylacrylamide (PHEA) or with (poly)dimethylacrylamide, all of which have been shown to minimize DNA/enzyme adsorption to glass. To minimize enzyme adsorption to the oil-aqueous interface, surfactants such as Tween 80 or Triton X-100 can be included in the PCR mix. Alternatively, the oil-surfactant formulation presented by Ghadessy et al. and used by Dressman et al., both referenced above, or other appropriate formulations for single DNA molecule amplification may be used.

Figures 11A, 11B:
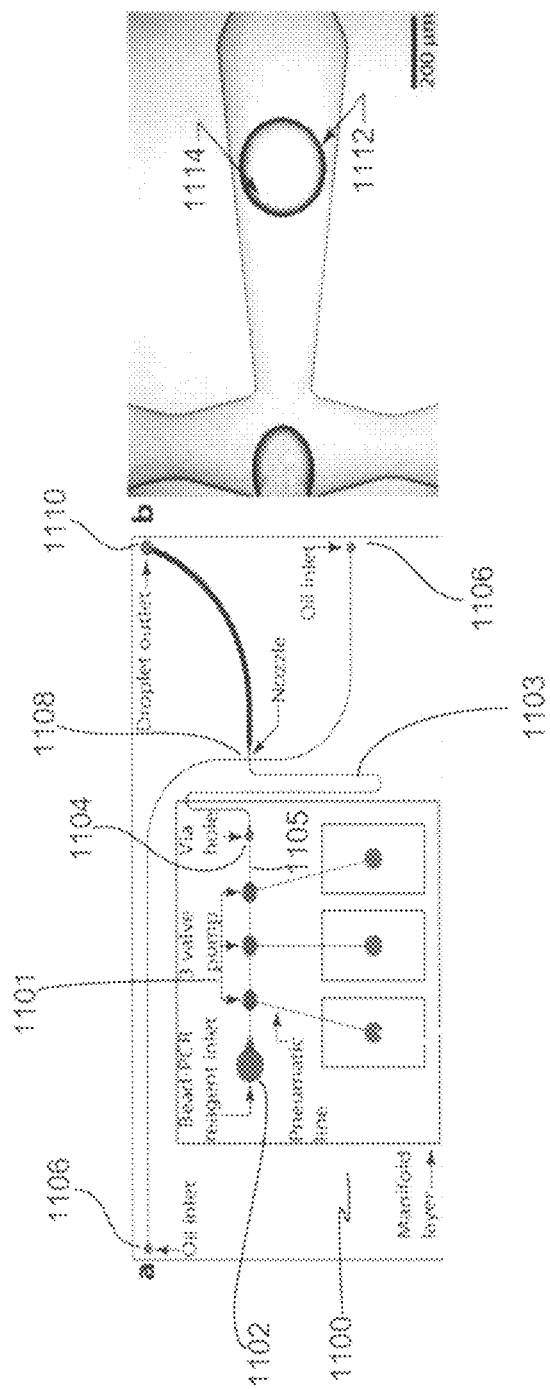
FIG. 11A is a diagrammatic representation of a microfabricated emulsion generator device layout that may be used in accordance with embodiments of the invention.
FIG. 11B is an optical micrograph of droplet formation at the nozzle. (A 34 μm diameter agarose bead is encapsulated in a 2.2 mL droplet.)

In order to manipulate products amplified from distinct DNA templates/cells in individual droplets, without the extreme loss of concentration caused by droplet lysis, primer functionalized microbeads may be incorporated in the droplets so that they are bound to the PCR progeny. Primer functionalized microbeads are mixed with PCR reagent at a stochastic limit dilution, and then introduced into droplets along with a single DNA molecule/cell at ratios that follow the Poisson distribution. See Margulies and Dressman, both referenced above, for a demonstration of this in conventional polydisperse emulsion PCR formats. This capability with the μDG is extremely useful because of the added advantages of efficient, uniform and large (>1 Kb) product amplification on beads. Flowing 22-44 μm diameter 6% agarose beads in droplets along with PCR reagent from a syringe into the device shown as in FIG. 10A, the beads tend to settle in the syringe as well as the chip input hole over time and do not get uniformly incorporated in the droplets. FIG. 11A shows a schematic of a μDG 1100 with an on-chip pump 1101 that has pulsatile flow that has been shown to facilitate bead movement in microchannels. (See Grover, et al., *Monolithic membrane valves and diaphragm pumps for practical large-scale integration into microfluidic devices*. Sensors & Actuators B 2003, 89, 315-323; and Grover, et al., *An Integrated Microfluidic Processor for Single Nucleotide Polymorphism-Based DNA Computing*. Lab-on-a-Chip 2005, 5, 1033-1040, both incorporated by reference herein). The use of an on-chip pump for bead-PCR mix flow has two additional advantages: (1) it obviates the use of syringe for PCR reagent and hence, negates the problem of DNA/enzyme adsorption to the syringe glass and (2) the pulsatile motion provides active control over the droplet formation process. The bead-PCR mix is pipetted into a reservoir (not shown) placed over a bead-PCR reagent inlet hole 1102 and withdrawn into the chip using the glass-PDMS-glass pump system described in Grover, Sensors and Actuators B, 2003, referenced above. A via hole 1104 transfers the bead-PCR mix from a glass-PDMS channel 1105 into an all-glass channel 1103. Emulsion oil is introduced directly into the all-glass channel at oil inlets 1106 using syringe pumps (not shown). The PDMS swells on contact with oil so it is kept spatially separated from the emulsion oil. Droplets are generated at a nozzle 1108 and routed out of the device at a droplet outlet 1110.

FIG. 11B presents an optical micrograph of an engineered 2.2 mL droplet 1112 containing a 34 μm agarose microbead 1114 formed with the μDG device shown in FIG. 11A. The pulsatile motion of on-chip pumping aids in droplet formation and provides a remarkable 1:1 correspondence between pumping frequency and droplet formation frequency. Hence the droplet volume is equal to the volume pumped every stroke, which in turn is proportional to the volume of the valves. This enables exact control over droplet volumes by fabricating corresponding size valve pumps.

Highly uniform 13 nL droplets collected from the μDG and imaged prior to thermal cycling were formed with 1.0 mm×1.4 mm valves, etched to a depth of 100 μm. A pumping frequency of 3.3 Hz was used and the combined oil flow rate was set to 4.0 μL/min. Large droplets (~5 mL and bigger) have reduced stability and merge on temperature cycling. Smaller (~4 mL) droplets (with beads) after 40 cycles of PCR, were formed by operating the on-chip pump at 5.5 Hz and setting the combined oil flow rate to 6.0 μL/min. Running the on-chip as well as the syringe pump faster helps modulate the droplet size but may introduce some polydispersity. The μDG device may incorporate valves with volumes proportional to 2~4 mL, such that droplet uniformity can be attained in the smaller size range by running the on-chip and syringe pumps at moderate speeds. Alternatively, bigger valves may be used to prevent beads from being tapped in valves with bifurcation of the bead-PCR reagent channel, which addresses multiple nozzles. This allows the volumetric flow rate to be dropped by half or one fourth in each of the downstream channels and at the same time allows for parallel droplet generation at two or four nozzles with a single bead-PCR mix input.

As indicated above, in certain embodiments, microbeads are used to confine and manipulate the PCR product from each droplet. There are two main criteria for choosing a microbead. First, the bead should support PCR amplification on its surface. Second, the surface area of the bead should be high enough to allow sufficient DNA (~100 attomoles) to amplify on each bead. Several types of beads have been successfully used as substrates for PCR, such as agarose beads, magnetic silica microbeads and polystyrene beads. All of these beads are commercially available with different size ranges. Agarose beads are the first choice because of their low density, hydrophilicity, minimal aggregation and high loading capacity. Magnetic silica microbeads allow simple and easy extraction of microbeads from the emulsion. However, the low loading capacity of these beads (low attomole range) might prevent their use for a sequencing project, where 100 attomoles of 1 kb DNA product is desired on the bead surface. Being more uniform in size, polystyrene is a good choice for quantification. A 9 μm polystyrene bead will have approximately 40 femtomoles of functional groups for surface conjugation. Overall, agarose beads have the highest number of functional groups per unit surface area. For example, agarose beads with a mean diameter of 34 μm have about 2 picomoles of functional groups for DNA coupling. Such a high loading capacity will ensure high PCR product yield on each bead.

Beads may be prepared in various manners. For example, N-hydroxysuccinimide ester (NHS)-activated agarose beads (34 μm mean diameter) (Amersham Biosciences) are washed with cold 0.1M HCl three times, cold $H_2O$ once, and cold 0.1M PBS (pH7.5) once to completely remove propanol in which the beads are stored. The beads and an amine labeled reverse primer are mixed in 0.1 M PBS (pH7.5) and incubated overnight for coupling. The primer concentration in the reaction will be set to about 4000 attomole/bead. Typically, as high as 50% of coupling yield can be reached for the reaction between an amine and NHS ester in aqueous condition. It is expected that about 2000 attomoles of primer can be coupled to a single bead. As the number of NHS groups on each bead is about 2 picomoles, the number of primers attached to each bead can be easily increased when necessary by adding higher concentration of primer in the coupling reaction. After coupling, the beads are washed 3 times with 0.1 M PBS to remove any unbound DNA and stored in pure water at 4° C. until needed. One potential problem of using the 34 μm agarose beads is their size polydispersity (ranging from 22-44 μm), which might result in significant variation in the number of DNA molecules generated on each bead even under controlled reaction conditions. This might not be a problem for sequencing and other qualitative applications. However, it could be a problem for quantitation. If this is found to be a problem, the size range of the beads may be narrowed by filtration methods.

To achieve optimum amplification yield and avoid the steric hindrance the solid surface (beads) poses to the polymerase in both PCR and sequencing reactions, the reverse primer will be conjugated to the beads via a polyethylene glycol linker. The length of polyethylene glycol (PEG) will be optimized carefully to achieve the highest PCR yield and longest sequencing read length. Optimization of the following PCR parameters: forward primer concentration in solution, reverse primer density on beads, polymerase concentration, annealing time and extension time may be performed. Flow Cytometry (FACS) analysis of the DNA yield on each bead will be used to evaluate and optimize PCR conditions. The optimization experiments will may be first carried out in solution without a microemulsion. Gel analysis of PCR production in solution may be performed to make sure no non-specific amplification occurs due to the altered PCR conditions. Recognizing the polymerase activity might decrease due to possible minor nonspecific adsorption of the enzyme to the oil-water interface, an optimization of PCR conditions in the droplet may also be performed with a focus on exploring the use of a surfactant, BSA or other additives to maintain optimum bead PCR efficiency.

The bead recovery process should remove oil and surfactants present in the emulsion completely so that they will not affect the downstream processing such as sequencing, genotyping, or quantitation of the DNA product on beads, with minimum lost of the secondary DNA strand that is hybridized to the bead bound strand (such as shown in FIG. 9A at 910. In certain embodiments, isopropyl alcohol is first used to dissolve the oil and surfactants. The solution is then passed through a 15 μm filter. The beads retained on the filter are washed three times with isopropyl alcohol, once with 100% ethanol and three times with 1×PCR buffer containing 1.5 mM $MgCl_2$. Results indicate that more than 70% of the beads can be recovered with about 90% of the DNA remaining double stranded.

Bead PCR efficiency in microemulsions that were generated with a traditional tissue lyser method and the effect of amplicon size on bead PCR efficiency was studied. The tissue lyser approach produced very small (~50 pL) emulsion droplets with a wide range of droplet sizes. Starting with 10 templates per bead, as high as 150 attomoles of 108 bp amplicon can be generated on each bead after 40 cycles of PCR. However, limited by the small volume of the droplets, the yield for long templates dropped significantly. This result illustrates an important fundamental limit of the current conventional bulk emulsion PCR techniques. About 23 attomoles of DNA product was found when the template length was increased to 545 bp. Performing PCR under the same conditions with ~4 mL-droplets generated with a μDG produced about 91 attomoles of 545 bp DNA product on each bead. These results establish that the bead PCR can be carried out in engineered emulsion droplets and that the droplets produced with the μDG device allow the amplification of long targets with high yield.

Figure 12:
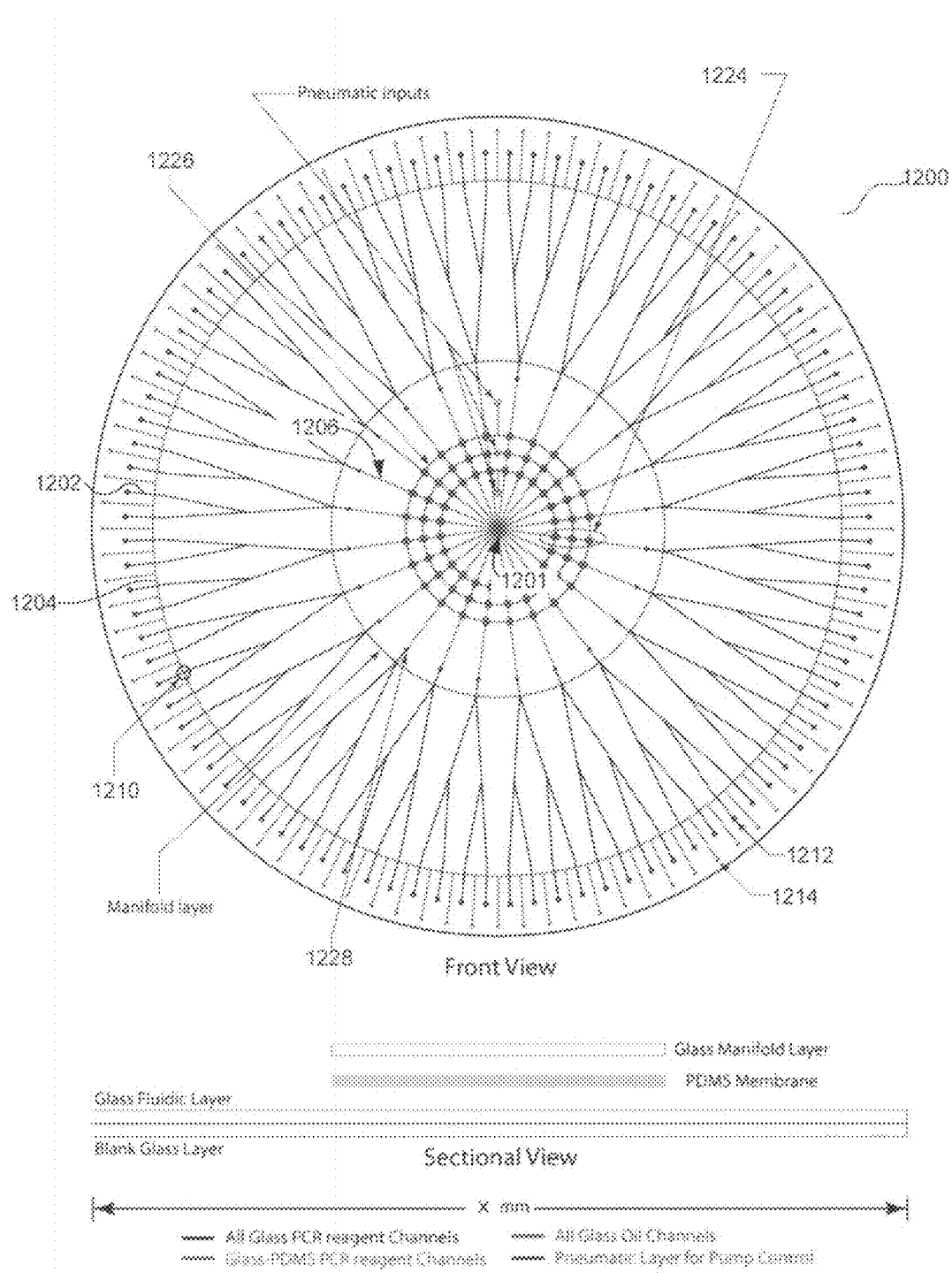
FIG. 12 is a diagrammatic representation of a 96 nozzle, high-throughput engineered microbead droplet emulsion generator with a single bead-PCR reagent inlet hole at the center.

FIG. 12 is diagrammatic representation of a polar arrayed μDG 1200 with 96 nozzles that are all supplied by a single bead-PCR reagent inlet 1201 at the center. Arrayed μDGs may be used for whole genome sequencing and other applications that require large numbers of nanoliter volume droplets. PCR reagent channels 1202, glass-PDMS PCR reagent channels 1206, and all glass oil channels 1204 are indicated. PCR droplet outlets are shown at 1212 and oil inlets at 1214. A via hole 1228 connects glass-PDMS channels to the all-glass channels. A pneumatic layer for pump control is indicated at 1208. Twenty-four 3-valve on-chip pumps (valve are indicated at 1224) are simultaneously controlled by 3 concentric pneumatic lines, indicated at 1226, to infuse reagent through bifurcating channels into 96 nozzles 1210. Each of the nozzles 96 is designed as the single nozzle 1108 in FIG. 11. Ninety-six oil inlet holes 1214, each addressing two oil channels, each allow symmetrical oil flow and uniform droplet formation at the nozzles. The operation of the 24 on-chip pumping devices which, in turn, each address 4 nozzles through channel bifurcation is similar to the device shown in FIG. 11A. The polar array format limits the bead-PCR mix inlet to one hole 1201 at the center but also combines the pneumatic control for the 24 pumps into just three lines. Ninety-six oil input holes 1214 allows oil phase flow into each of the two adjacent nozzles, thereby aiding in symmetrical and focused droplet release. All the oil input and droplet output connections may be made through a circular custom interconnect, similar to that shown in FIG. 10A. Five infuse/withdraw syringe pumps (not shown) (Model#702006, Harvard Apparatus) with ten 1 mL gastight syringe holders each and a flow splitting connection (Upchurch Scientific) for all the syringes (1700 series, Hamilton Company) allow simultaneous and continuous addressing of the 96 oil lines. Alternatively, oil flow can be split into multiple lines within the microfabricated device, thus reducing the number of syringe pumps required. In the arrayed μDG, as all the on-chip pumps are simultaneously addressed by the three pneumatic lines, in certain embodiments, about 10-11 droplets/sec are generated at each of the 96 nozzles, enabling production of 1000 nanoliter volume droplets per second per wafer.

Figure 13:
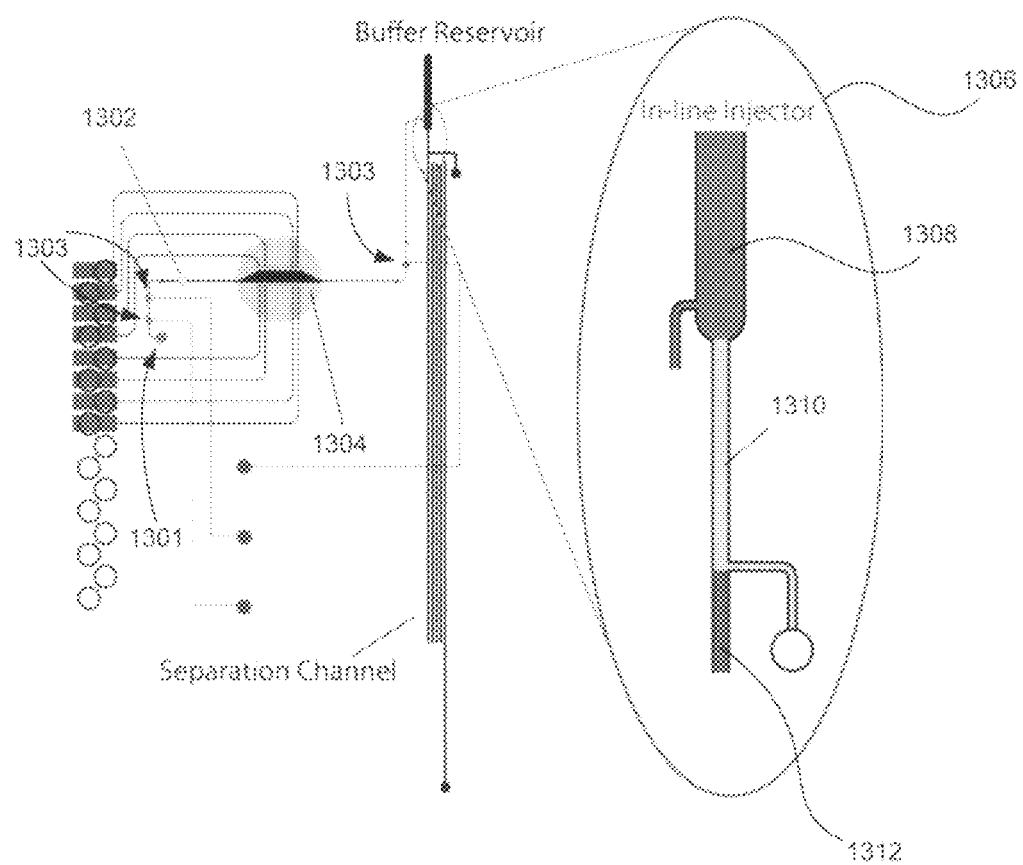
FIG. 13 is a diagrammatic representation of an in-line integrated bioprocessor for sequencing from single clonal bead-templates.

FIG. 13 shows a diagrammatic representation of device that includes a bead detector 1302, thermal cycling reactor 1304 and an inline injector 1306, including a sample containment region/buffer reservoir 1308 and a capture region 1310. The bead detector 1302, e.g., based on light scattering or fluorescence, is positioned just before the reactor 1304, and valves are positioned on either side of the reactor to trap a single bead inside. The device allows quantitative injection of the products generated from thermal cycling a single clonal bead and thereby enabling sequencing from the 75 to over 100 attomoles of DNA template per bead. To introduce a bead into the integrated chip, a dilute solution of beads is placed in an inlet reservoir 1301 and pumped with PDMS pumps 1303 toward the thermal cycling chamber. The bead detector 1302 is used to reveal when a bead has passed the detector and entered the chamber. By closing valves on either side of the chamber, with the appropriate delay determined by the flow rate, the bead is trapped inside for cycle sequencing. Since the PDMS pumps are positive displacement and quantitative, the bead is pumped precisely from the detector to the chamber. The extension fragments thus generated by thermal cycling the trapped bead in the chamber will be pumped to the buffer reservoir from where they will be captured and injected into a separation channel 1312 in a manner described above with reference to FIGS. 2A-2E. The bead detector may take various designs. For example, a visible light scattering detector could be used. This would consist of a 633 nm HeNe laser cylindrically focused on the channel. Bead passage is sensed by looking at changes in the scatter signal caused by the scattering and or refraction absorption or fluorescence of the beam caused by the passing beads with a photodiode. However, the agarose beads are almost transparent, so it is possible they will not provide a strong signal. Alternatively, an intercalating dye, such as that which binds to the dsDNA on the bead at a stoichiometry of one dye per ten bp, may be used. By configuring the chip in a simple fluorescence microscope with 488 nm laser excitation, the TO fluorescence can be readily detected. Dyed beads for fluorescent bead detection may also be used as long as the dye choice does not interfere with clonal detection. The scattering sensor could be placed at the start of a distribution channel that has valves that can direct the detected bead to any of multiple such reaction systems arrayed along the distribution channel.

While the invention has been particularly shown and described with reference to specific embodiments, it will also be understood by those skilled in the art that changes in the form and details of the disclosed embodiments may be made without departing from the spirit or scope of the invention. For example, the embodiments described above may be implemented using a variety of materials. Therefore, the scope of the invention should be determined with reference to the appended claims.

What is claimed is:

1. A microfabricated structure comprising:
   a) a sample channel defining a flow path between a first location and a second location and comprising:
      i. a capture channel region comprising a capture matrix;
      ii. a separation channel region, wherein the structure of the capture channel region and the separation channel region is characterized by at least one of the following: 1) the capture channel region contacts that separation channel region without intervening channels or 2) the capture channel region and at least a portion of the separation channel region are arranged in a continuous line along the sample channel, said line being a straight line or a line that deviates from 180° by no more than about +/−45°;
   b) a first electrode in electrical communication with the first location;
   c) a waste port in fluid communication with the capture channel region;
   d) a second electrode in electrical communication with the waste port, wherein a voltage applied between the first and second electrodes moves charged molecules through the capture channel region to the waste port; and
   e) a third electrode in electrical communication with the second location, wherein a voltage applied between the first and third electrodes moves charged molecules from the capture channel region through the separation channel region, wherein the sample channel, first electrode, second electrode and third electrode are all integrated into the same microfabricated structure.

2. The microfabricated structure of claim 1 wherein the capture matrix supports a capture compound having a selective affinity for the analyte.

3. The microfabricated structure of claim 1 wherein the capture matrix forms a purified and concentrated sample plug.

4. The microfabricated structure of claim 1 wherein the waste port is connected to a sidearm located downstream of the capture channel region.

5. The microfabricated structure of claim 1 wherein the capture matrix comprises at least one of a gel, immobilized beads, a porous monolith, dense posts, pillars and weirs.

6. The microfabricated structure of claim 1 wherein the capture matrix comprises a UV-polymerized gel.

7. The microfabricated structure of claim 1 further comprising a sample channel region configured to contain an unpurified sample of an analyte, wherein the sample channel region includes a thermal cycler chamber to produce extension fragments from a sequencing template.

8. The microfabricated structure of claim 1 wherein the analyte comprises extension fragments from a DNA or RNA template and the capture matrix supports an oligonucleotide complementary to a portion of the extension fragments.

9. The microfabricated structure of claim 1 further comprising a sample channel region configured to contain an unpurified sample of an analyte, wherein the sample channel region has a volume between about 10-1000 nanoliters.

10. The microfabricated structure of claim 1 wherein the capture channel region has a volume between about 1-1000 nanoliters.

11. The microfabricated structure of claim 1 wherein the capture channel region has a volume between about 1-100 nanoliters.

12. The microfabricated structure of claim 1 further comprising: a radial array of inline injection and separation elements, each element comprising: a sample channel region for containing an unpurified sample of an analyte; a capture channel region containing a capture matrix for forming a concentrated sample plug, wherein said capture matrix has a selective affinity for the analyte; a separation channel region to receive the sample plug and separate the analyte, wherein the structure of the capture channel region and the separation channel region is characterized by at least one of the following: 1) the capture channel region contacts that separation channel region without intervening channels or 2) the capture channel region and at least a portion of the separation channel region are arranged in a continuous line along the sample channel, said line being a straight line or a line that deviates from 180° by no more than about +/−45°;
   a reagent distribution channel linking the sample channel regions; a capture matrix distribution channel linking the capture channel regions; and an anode common to all elements.

13. The microfabricated structure of claim 12 wherein the reagent distribution channel is configured to distribute microreactor elements each of which carries multiple copies of a unique clonal sequencing template into the sample channel regions such that only one microreactor element will pass into one sample channel region.

14. The microfabricated structure of claim 1, further comprising a plurality of sequencing elements, each element comprising:
   a thermal cycling reactor for producing forward and reverse extension fragments from a sequencing template;
   a forward capture channel region containing a forward capture matrix for concentrating forward extension fragments, wherein said forward capture matrix supports an oligonucleotide that selectively hybridizes to the forward extension fragments;
   a reverse capture channel region containing a reverse capture matrix for concentrating reverse extension fragments, wherein said reverse capture matrix supports an oligonucleotide that selectively hybridizes to the reverse extension fragments;
   a forward separation channel to separate the forward extension fragments; and
   a reverse separation channel to separate the reverse extension fragments, wherein the forward and reverse capture channel regions and forward and reverse separation channel regions are all integrated into the same microfabricated structure.

15. The microfabricated structure of claim 14, further comprising:
   a reagent distribution channel to distribute microreactor elements carrying multiple copies of a clonal sequencing template into the plurality of thermal cycling chambers, wherein each thermal cycling chamber receives exactly one unique clonal sequencing template; and
   a forward capture matrix distribution channel to distribute forward capture matrix material into the forward capture channel region.

16. The microfabricated structure of claim 15, further comprising:
   a reverse capture matrix distribution channel to distribute reverse capture matrix material into the reverse capture channel region.

17. The microfabricated structure of claim 15, further comprising a transfer channel connecting the forward and reverse capture channel regions.

18. The microfabricated structure of claim 15 further comprising passive valving to distribute the microreactor elements into the plurality of thermal cycling chambers.

19. The microfabricated structure of claim 15 further comprising active valving to distribute the microreactor elements into the plurality of thermal cycling chambers.

20. The microfabricated structure of claim 1 further comprising:
a distribution channel configured to distribute microreactor elements carrying multiple copies of a clonal sequencing template into each of a plurality of channels such that only one microreactor element will pass into one channel, wherein each channel comprises a thermal cycling chamber connected to a purification chamber connected to a component separation channel, wherein:
thermal cycling extension fragments are produced from a microreactor element in the thermal cycling chambers;
the purification chambers are configured to capture and concentrate the extension fragments; and
the component separation channels are configured to analyze the extension fragments.

21. The microfabricated structure of claim 1 wherein the capture channel region and the separation channel region are part of the same etched main channel.

22. The microfabricated structure of claim 1 wherein the capture channel region and the separation channel region share a common axis.

23. A process of introducing an analyte in a sample to a separation channel comprising:
providing a microfabricated structure comprising:
a) a sample channel defining a flow path between a first location and a second location and comprising:
i. a capture channel region comprising a capture matrix;
ii. a separation channel region, wherein the structure of the capture channel region and the separation channel region is characterized by at least one of the following: 1) the capture channel region contacts that separation channel region without intervening channels or 2) the capture channel region and at least a portion of the separation channel region are arranged in a continuous line along the sample channel, said line being a straight line or a line that deviates from 180° by no more than about +/−45°;
b) a first electrode in electrical communication with the first location;
c) a waste port in fluid communication with the capture channel region;
d) a second electrode in electrical communication with the waste port, wherein a voltage applied between the first and second electrodes moves charged molecules through the capture channel region to the waste port; and
e) a third electrode in electrical communication with the second location, wherein a voltage applied between the first and third electrodes moves charged molecules from the capture channel region through the separation channel region;
introducing a sample containing an analyte to the sample channel region;
driving the analyte in the sample to the capture channel region containing the capture matrix, said matrix having a selective affinity for the analyte;
forming a concentrated sample plug in the capture channel region; and
inline injecting the concentrated sample plug from the capture channel region into the separation channel region.

24. The process of claim 23 further comprising forming a purified sample plug in the capture channel region.

25. The process of claim 23 wherein the sample channel region comprises a thermal cycling reactor and introducing a sample containing an analyte to the sample channel region comprises forming extension fragments from a sequencing template in the thermal cycling reactor.

26. The process of claim 23 wherein the analyte comprises extension fragments produced from a sequencing template and forming a concentrated sample plug in the capture channel region comprises selective hybridization of at least some of the extension fragments to oligonucleotides in the capture matrix.

27. The process of claim 23 further comprising thermally releasing the sample plug from the capture matrix prior to injection.

28. A process for performing sequencing comprising:
providing a microfabricated structure comprising:
a) a sample channel defining a flow path between a first location and a second location and comprising:
i. a capture channel region comprising a capture matrix;
ii. a separation channel region, wherein the structure of the capture channel region and the separation channel region is characterized by at least one of the following: 1) the capture channel region contacts that separation channel region without intervening channels or 2) the capture channel region and at least a portion of the separation channel region are arranged in a continuous line along the sample channel, said line being a straight line or a line that deviates from 180° by no more than about +/−45°;
b) a first electrode in electrical communication with the first location
c) a waste port in fluid communication with the capture channel region;
d) a second electrode in electrical communication with the waste port, wherein a voltage applied between the first and second electrodes moves charged molecules through the capture channel region to the waste port; and
e) a third electrode in electrical communication with a second location, wherein a voltage applied between the first and third electrodes moves charged molecules from the capture channel region through the separation channel region;
distributing microreactor elements with DNA sequencing templates into thermal cycling chambers, wherein each microreactor element has multiple clonal copies of a single unique sequencing template;
producing thermal cycling extension fragments from the microreactor elements carrying multiple copies of a sequencing template;
forming a concentrated sample plug of the extension fragments in the capture channel region comprising the capture matrix;
inline injecting the sample plug from the capture matrix into the separation channel; and
separating the extension fragments in the separation channel.

29. The process of claim 28 further comprising introducing capture matrix material into the capture channel region and photo-polymerizing at least a portion of the capture matrix material to produce the capture matrix.

30. The process of claim 28 wherein the microreactor element includes a microcarrier element which carries the multiple copies of the clonal sequencing template.

31. The process of claim 28 wherein the microreactor element is a bolus or a microemulsion droplet.

32. The process of claim 28 wherein the microreactor element includes a microbead carrying the multiple copies of the clonal sequencing template.

33. The process of claim 28 wherein the distributing step is done such that only one microreactor element will pass into one thermal cycling chamber.

34. The process of claim 33 further including using a valve at an exit port of the thermal cycling chambers to ensure that only one microreactor element will flow into one thermal cycling chamber.

35. The process of claim 28 further comprising opening a single microvalve in a distribution channel to distribute reagent containing microelements to the thermal cycling chambers via the distribution channel.

36. The process of claim 28 further comprising sensing the presence of a microelement having multiple clonal copies of DNA sequencing template in a distribution channel and directing that microelement to a thermal cycling reactor.

37. A process for performing sequencing comprising:
providing a microfabricated structure comprising:
  a) a plurality of sample channels each comprising:
    i. a thermal cycling chamber;
    ii. a capture channel region comprising a capture matrix;
    iii. a separation channel region, wherein the structure of the capture channel region and the separation channel region is characterized by at least one of the following: 1) the capture channel region contacts that separation channel region without intervening channels or 2) the capture channel region and at least a portion of the separation channel region are arranged in a continuous line along the sample channel, said line being a straight line or a line that deviates from 180° by no more than about +/−45°;
  b) a first electrode in electrical communication with a first end of each of the plurality of sample channels;
  c) one or more waste ports in fluid communication with the capture channel regions;
  d) a second electrode in electrical communication with the each of the one or more waste ports, wherein a voltage applied between the first and second electrodes moves charged molecules through a capture channel region to a waste port; and
  e) a third electrode in electrical communication with a second end of each of the sample channels, wherein a voltage applied between the first and third electrodes moves charged molecules from the capture channel region through the separation channel region;
distributing microreactor elements with DNA sequencing templates into thermal cycling chambers, wherein each microreactor element has multiple clonal copies of a single unique sequencing template;
producing thermal cycling extension fragments from the microreactor elements carrying multiple copies of a sequencing template;
forming a concentrated sample plug of the extension fragments in a capture channel region comprising a capture matrix; and
injecting the sample plug from the capture matrix into a separation channel, wherein at least about 50% of the extension fragments produced are injected into the separation channel.

38. The process for performing sequencing of claim 37, wherein at least about 70% of the extension fragments produced are injected into the separation channel.

39. The process for performing sequencing of claim 37, wherein at least about 80% of the extension fragments produced are injected into the separation channel.

40. The process for performing sequencing of claim 37, wherein at least about 90% of the extension fragments produced are injected into the separation channel.

41. A method comprising:
providing a microfabricated structure comprising:
  a) a sample channel defining a flow path between a first location and a second location and comprising:
    i. a capture channel region comprising a capture matrix;
    ii. a separation channel region, wherein the structure of the capture channel region and the separation channel region is characterized by at least one of the following: 1) the capture channel region contacts that separation channel region without intervening channels or 2) the capture channel region and at least a portion of the separation channel region are arranged in a continuous line along the sample channel, said line being a straight line or a line that deviates from 180° by no more than about +/−45°;
  b) a first electrode in electrical communication with the first location;
  c) a waste port in fluid communication with the capture channel region;
  d) a second electrode in electrical communication with the waste port, wherein a voltage applied between the first and second electrodes moves charged molecules through the capture channel region to the waste port; and
  e) a third electrode in electrical communication with the second location, wherein a voltage applied between the first and third electrodes moves charged molecules from the capture channel region through the separation channel region;
providing in the sample channel a sample comprising analyte molecules and non-analyte molecules;
applying an electrical potential across a fluid path comprising a capture channel region and the waste port, wherein non-analyte molecules are moved by the electrical potential to the waste port;
releasing captured analyte molecules from the capture matrix;
applying an electrical potential across a second fluid path comprising the capture channel region and the separation channel region to move analyte molecules through the separation channel, whereby analyte molecules are resolved; and
detecting the resolved analyte molecules.

42. The method of claim 41 wherein releasing comprises increasing the temperature of the affinity capture matrix.

* * * * *